(12) United States Patent
Currie et al.

(10) Patent No.: US 7,393,848 B2
(45) Date of Patent: Jul. 1, 2008

(54) CERTAIN HETEROCYCLIC SUBSTITUTED IMIDAZO[1,2-A]PYRAZIN-8-YLAMINES AND METHODS OF INHIBITION OF BRUTON'S TYROSINE KINASE BY SUCH COMPOUNDS

(75) Inventors: Kevin S. Currie, North Branford, CT (US); Robert W. DeSimone, Durham, CT (US); Scott A. Mitchell, East Haven, CT (US); Douglas A. Pippin, Branford, CT (US)

(73) Assignee: CGI Pharmaceuticals, Inc., Branford, CT (US)

( * ) Notice: Subject to any disclaimer, the term of this patent is extended or adjusted under 35 U.S.C. 154(b) by 172 days.

(21) Appl. No.: 10/883,646

(22) Filed: Jun. 30, 2004

(65) Prior Publication Data

US 2005/0101604 A1    May 12, 2005

Related U.S. Application Data

(60) Provisional application No. 60/484,014, filed on Jun. 30, 2003.

(51) Int. Cl.
| | | |
|---|---|---|
| A01N 43/58 | (2006.01) | |
| A01N 43/60 | (2006.01) | |
| A61K 31/50 | (2006.01) | |
| A61K 31/495 | (2006.01) | |
| C07D 471/00 | (2006.01) | |
| C07D 487/00 | (2006.01) | |
| C07D 491/00 | (2006.01) | |
| C07D 495/00 | (2006.01) | |

(52) U.S. Cl. ........................ 514/249; 544/350
(58) Field of Classification Search ............ 514/249; 544/350

See application file for complete search history.

(56) References Cited

U.S. PATENT DOCUMENTS

| | | | |
|---|---|---|---|
| 5,593,997 A | 1/1997 | Dow et al. | |
| 5,658,857 A | 8/1997 | Andree et al. | |
| 5,783,576 A | 7/1998 | Roos et al. | |
| 6,919,341 B2 * | 7/2005 | Paruch et al. | 514/249 |
| 2003/0212073 A1 | 11/2003 | Currie et al. | |
| 2004/0063715 A1 | 4/2004 | Paruch et al. | |
| 2004/0067951 A1 | 4/2004 | DeSimone et al. | |
| 2004/0072835 A1 | 4/2004 | Paruch et al. | |
| 2004/0220189 A1 | 11/2004 | Sun et al. | |

FOREIGN PATENT DOCUMENTS

DE    0 43 37 609    5/1995

(Continued)

OTHER PUBLICATIONS

Al-Dabbagh and Smith, "Species differences in oxidative drug metabolism: some basic considerations." Archives of toxicology. Supplement. Archiv fur Toxikologie. supplement, vol. 7, pp. 219-231 (1984).*

Hans Bundgaard, Design of Prodrugs, p. 1. © 1985 Elsevier Science Publishers.*

(Continued)

*Primary Examiner*—Zachary C Tucker
(74) *Attorney, Agent, or Firm*—Millen, White, Zelano & Branigan, P.C.

(57) ABSTRACT

Compounds of Formula I

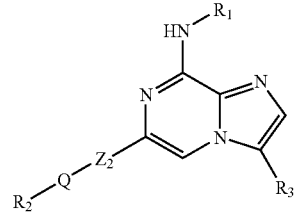

(Formula I)

and all pharmaceutically acceptable forms thereof, are described herein.

The variables $R_1$, $R_2$, $R_3$, $Z_2$, and Q, shown in Formula I are defined herein.

Pharmaceutical compositions containing one or more compounds of Formula I, or a pharmaceutically acceptable form of such compounds, and one or more pharmaceutically acceptable carriers, excipients, or diluents are provided herein.

Methods of treating patients suffering from certain diseases responsive to inhibition of tyrosine kinase activity are also given. In certain embodiments the diseases are responsive to inhibition of Btk activity and/or B-cell proliferation. Such methods comprise administering to such patients an amount of a compound of Formula I effective to reduce signs or symptoms of the disease. These diseases include cancer, an autoimmune and/or inflammatory disease, or an acute inflammatory reaction. Thus methods of treatment include administering a sufficient amount of a compound or salt as provided herein to decrease the symptoms or slow the progression of these diseases.

Other embodiments include methods of treating other animals, including livestock and domesticated companion animals, suffering from a disease responsive to inhibition of kinase activity.

Methods of treatment include administering a compound of Formula I as a single active agent or administering a compound of Formula I in combination with one or more other therapeutic agent.

A method for determining the presence of Btk in a sample, comprising contacting the sample with a compound or form thereof of Formula I under conditions that permit detection of Btk activity, detecting a level of Btk activity in the sample, and therefrom determining the presence or absence of Btk in the sample.

50 Claims, No Drawings

FOREIGN PATENT DOCUMENTS

| | | |
|---|---|---|
| EP | 0 480 713 | 4/1992 |
| WO | WO 88/04298 | 6/1988 |
| WO | WO 95/12594 | 5/1995 |
| WO | WO 96/04298 | 2/1996 |
| WO | WO 96/34866 | 11/1996 |
| WO | WO 99/28322 | 6/1999 |
| WO | WO 01/27119 | 4/2001 |
| WO | WO 02/10170 | 2/2002 |
| WO | WO 02/30428 | 4/2002 |
| WO | WO 02/060492 | 8/2002 |
| WO | WO 03/089434 | 10/2003 |
| WO | WO 2004/022562 | 3/2004 |
| WO | WO 2004/026310 | 4/2004 |
| WO | WO 2004/026877 | 4/2004 |
| WO | WO 2004/072080 | 8/2004 |
| WO | WO 2004/072081 | 8/2004 |

OTHER PUBLICATIONS

Richard B. Silverman, The Organic Chemistry of Drug Design and Drug Action, pp. 352-400. © 1992 Academic Press, Inc.*
Vippagunta et al, "Crystalline Solids" Advanced Drug Delivery Reviews, vol. 48, pp. 3-26 (2001).*
Gavezzotti, "Are Crystal Structures Predictable?" Accounts of Chemical Research, vol. 27, pp. 309-314 (1994).*
Vassilev and Uckun "Therapeutic Potential of Inhibiting Bruton's Tyrosine Kinase, (BTK)" Current Pharmaceutical Design, vol. 10, pp. 1757-1766 (2004).*
Ding et al. (2002) "A Combinatorial Scaffold Approach toward Kinase-Directed Heterocycle Libraries," J. Am. Chem. Soc., 124(8): 1594-1596.
Hanks (Apr. 1, 1994) "Hanks Classification: Protein Kinase Classification, provided by Steven K. Hanks," pp. 1-4, from http://pkr.sdsc.edu/html/pk_classification/pk_catalytic/pk_hanks_class.html.
Jeffrey et al. (1998) "Phosphodiesterase III and V Inhibitors on Pulmonary Artery from Pulmonary Hypertensive Rats: Differences Between Early and Established Pulmonary Hypertension," J. Cardiovascular Pharmacology, 32:213-219.
Lumma Jr. et al. (1983) "Piperazinylimidazo[1,2-a]pyrazines with Selective Affinity for in Vitro alpha-Adrenergic Receptor Subtypes," J. Med. Chem., 26:357-363.
"Protein Kinases in Disease," references produced from a Sep. 24, 1997, search of the On-line Meddelian Inheritance in Man (OMIM) database, pp. 1-11, from http://bioinformatics.weizmann.ac.il/Kinases/pkr/pk_medicine.html.
Stenberg et al. (2000) "KinMutBase, a database of human disease-causing protein kinase mutations," Nucleic Acids Research, 28(1):369-371.
Vitse et al. (1999) "New Imidazo[1,2-*a*]pyrazine Derivatives with Brochodilatory and Cyclic Nucleotide Phosphodiesterase Inhibitory Activities," Bioorganic & Medicinal Chemistry, 7: 1059-1065.
Restriction Requirement dated Oct. 20, 2004, for U.S. Appl. No. 10/419,682, filed Apr. 21, 2003.
International Search Report dated Oct. 22, 2003, for Application No. PCT/US03/1222, International filing date Apr. 21, 2003.
Written Opinion dated Dec. 5, 2003, for Application No. PCT/US03/12222, International filing date Apr. 21, 2003.
Second Written Opinion dated Apr. 13, 2004, for Application No. PCT/US03/12222, International filing date Apr. 21, 2003.
International Preliminary Examination Report dated Aug. 3, 2004, for Application No. PCT/US03/12222, International filing date Apr. 21, 2003.
International Search Report dated Feb. 9, 2004, for Application No. PCT/US03/28329, International filing date Sep. 9, 2003.
Written Opinion dated Jul. 6, 2004, for Application No. PCT/US03/28329, International filing date Sep. 9, 2003.
International Preliminary Examination Report dated Oct. 27, 2004, for Application No. PCT/US03/28329, International filing date Sep. 9, 2003.
International Search Report and Written Opinion dated Jul. 7, 2004, for Application No. PCT/US2004/003922, International filing date Feb. 10, 2004.
International Search Report and Written Opinion dated Jul. 7, 2004, for Application No. PCT/US2004/003923, International filing date Feb. 10, 2004.
International Search Report and Written Opinion dated Dec. 8, 2004, for Application No. PCT/US2004/021150, International filing date Jun. 30, 2004.
Tsukada, S., et al., *Deficient expression of a B cell cytoplasmic kinase in human X-linked agammaglobulinemia*. Cell, 1993. 72: p. 279-290.
Vetrie, D., et al., *The gene involved in X-linked agammaglobulinemia is a member of the src family of protein kinases*. Nature, 1993. 361: p. 226-233.
Steinberg, B.J., et al., *Ability of the xid gene to prevent autoimmunity in (NZB X NZW)F1 mice during the course of their natural history, after polyclonal stimulation, or following immunization with DNA*. J Clin Invest, 1982. 70(3): p. 587-597.
Smith, H.R., T.M. Chused, and A.D. Steinberg, *The Effect of the X-linked Immune Deficiency Gene (xid) upon the Y Chromosome-Related Disease of BXSB Mice*. The Journal of Immunology, 1983. 131: p. 1257-1262.
Steinberg, E.B., et al., *Studies of Congenic MRL-lpr/lpr.xid Mice*. The Journal of Immunology, 1983. 131(2789-2795).
Fieser, T.M., et al., *Abrogation of Murine Lupus by the xid Gene is Associated with Reduced Responsiveness of B Cells to T-Cell-Helper Signals*. Cellular Immunology, 1984. 87: p. 708-713.
Steinberg, A.D., et al., *Systemic Lupus Erythematosus: Insights from Animal Models*. Annals of Internal Medicine, 1984. 100: p. 714-727.
Reeves, J.P. and A.D. Steinberg, *Effect of the xid Gene on Graft-versus-Host-Induced Autoantibody Production in Nonautoimmune Mice*. Clinical Immunology and Imunopathology, 1985. 36: p. 320-329.
Jansson, L. and R. Holmdahl, *Genes on the X chromosome affect development of collagen-induced arthritis in mice*. Clin Exp Immunol, 1993. 94: p. 459-465.
Zhao, Y.X., et al., *Mice with the xid B cell defect are less susceptible to developing Staphylococcus aureus-induced arthritis*. J Immunol., 1995. 155(4): p. 2067-76.
Farrar, J.E., J. Rohrer, and M.E. Conley, *Neutropenia in X-linked agammaglobulinemia*. Clin Immunol Immunopathol, 1996. 81(3): p. 271-6.
Hata, D., et al., *Involvement of Bruton's tyrosine kinase in FcepsilonRI-dependent mast cell degranulation and cytokine production*. J Exp Med, 1998. 187(8): p. 1235-47.
Svensson, L., et al., *B cell-deficient mice do not develop type II collagen-induced arthritis (CIA)*. Clin Exp Immunol, 1998. 111: p. 521-526.
Mukhopadhyay, S., et al., *Macrophage effector functions controlled by Bruton's tyrosine kinase are more crucial than the cytokine balance of T cell responses for microfilarial clearance*. J Immunol, 2002. 168(6): p. 2914-21.
Whyburn, L.R., et al., *Reduced dosage of Bruton's tyrosine kinase uncouples B cell hyperresponsiveness from autoimmunity in lyn-/- mice*. J Immunol, 2003. 171(4): p. 1850-8.
Feldhahn, N., et al., *Deficiency of Bruton's tyrosine kinase in B cell precursor leukemia cells*. Proc Natl Acad Sci U S A., 2005. 102(37): p. 13266-71. Epub Sep. 2, 2005.
Feldhahn, N., et al., *Mimicry of a constitutively active pre-B cell receptor in acute lymphoblastic leukemia cells*. J Exp Med., 2005. 201(11): p. 1837-52.
Irish, J.M., et al., *Altered B-cell receptor signaling kinetics distinguish human follicular lymphoma B cells from tumor-infiltrating nonmalignant B cells*. Blood., 2006. 108(9): p. 3135-42. Epub Jul. 11, 2006.
Vassilev, A.O., et al., *Therapeutic Potential of Inhibiting Bruton's Tyrosine Kinase, (BTK)*, Current Pharmaceutical Design, 10, 2004, pp. 1757-1766.

* cited by examiner

CERTAIN HETEROCYCLIC SUBSTITUTED IMIDAZO[1,2-A]PYRAZIN-8-YLAMINES AND METHODS OF INHIBITION OF BRUTON'S TYROSINE KINASE BY SUCH COMPOUNDS

CROSS-REFERENCE TO RELATED APPLICATIONS

This application claims priority to U.S. provisional application 60/484,014 filed Jun. 30, 2003, which is hereby incorporated by reference in their entirety.

FIELD OF INVENTION

Certain heterocyclic substituted imidazo[1,2-a]pyrazin-8-ylamine and related compounds, which are inhibitors of tyrosine kinase activity, including Bruton's tyrosine kinase (Btk) activity, are provided herein. Certain compounds provided herein are highly active and/or specific inhibitors of Btk activity. Pharmaceutical compositions comprising such compounds, and methods of using certain heterocyclic substituted imidazo[1,2-a]pyrazin-8-ylamine and related compounds to treat a variety of diseases responsive to inhibition of Btk activity and/or inhibition of B-cell proliferation, are also disclosed. Additionally, methods for using such compounds as probes for the detection and/or localization of Btk in biological samples are given.

BACKGROUND

Protein kinases, the largest family of human enzymes, encompass well over 500 proteins. Kinases play critical roles in signaling pathways controlling fundamental cellular processes such as proliferation, differentiation, and death (apoptosis). Abnormal kinase activity has been implicated in a wide range of diseases, including multiple cancers and autoimmune and inflammatory diseases. The multifaceted role of kinases in key cell signaling pathways provides a significant opportunity to identify novel drugs targeting kinases and signaling pathways. Diseases mediated by kinase activity include, but are not limited to, diseases characterized in part by abnormal levels of cell proliferation (i.e. tumor growth), programmed cell death (apoptosis), cell migration and invasion, and angiogenesis associated with tumor growth.

Because kinases are key regulators they are ideal drug design targets. Inhibitors of kinases are among the most important classes of pharmaceutical compounds known. Highly specific, cell-permeable inhibitors of one or more individual kinases are useful for the treatment of various kinase-implicated diseases. Kinase inhibiting compounds are additionally useful for the systematic investigation of the cellular function of one or more kinases, and thus, provide valuable tools for the identification of various kinases of therapeutic interest.

Bruton's Tyrosine Kinase (Btk) is a member of the Tec family of tyrosine kinases, and is a critical regulator of early B-cell development as well as mature B-cell activation, signaling and survival.

B-cell signaling through the B-cell receptor (BCR) leads to a wide range of biological outputs, which in turn depend on the developmental stage of the B-cell. The magnitude and duration of BCR signals must be precisely regulated. Aberrant BCR-mediated signaling can cause deregulated B-cell proliferation and/or the formation of pathogenic autoantibodies leading to multiple autoimmune and/or inflammatory diseases. Mutation of Btk in humans results in X-linked agammaglobulinemia (XLA). This disease is associated with the impaired maturation of B-cells, diminished immunoglobulin production, compromised T-cell-independent immune responses and marked attenuation of the sustained calcium sign upon BCR stimulation.

Evidence for the role of Btk in autoimmune and/or inflammatory disease has been established in Btk-deficient mouse models. For example, in standard murine preclinical models of systemic lupus erythematosus (SLE), Btk deficiency has been shown to result in a marked amelioration of disease progression. Moreover, Btk deficient mice are also resistant to developing collagen-induced arthritis and are less susceptible to Staphylococcus-induced arthritis.

A large body of evidence supports the role of B-cells and the humoral immune system in the pathogenesis of autoimmune and/or inflammatory diseases. Protein-based therapeutics (such as Rituxan) developed to deplete B-cells, represent an important approach to the treatment of a number of autoimmune and/or inflammatory diseases. Because of Btk's role in B-cell activation, inhibitors of Btk are useful as inhibitors of B-cell mediated pathogenic activity (such as autoantibody production).

Btk is also expressed in mast cells and monocytes and has been shown to be important for the function of these cells. For example, Btk deficiency in mice is associated with impaired IgE-mediated mast cell activation (marked diminution of TNFα and other inflammatory cytokine release), and greatly reduced TNFα production by activated monocytes.

Thus, inhibition of Btk activity is useful for the treatment of autoimmune and/or inflammatory diseases such as: SLE, rheumatoid arthritis, multiple vasculitides, idiopathic thrombocytopenic purpura (ITP), myasthenia gravis, and asthma. In addition, Btk has been reported to play a role in apoptosis, thus inhibition of Btk activity is useful for the treatment of B-cell lymphoma and leukemia.

Agents capable of inhibiting Btk kinase activity are highly desirable for the treatment of a variety of diseases, including cancer, an autoimmune and/or inflammatory disease, or an acute inflammatory reaction. Specific, cell-penetrating, small molecule, non-peptide antagonists of Btk are of particular value for such therapies. Such compounds are also useful for the systematic investigation of the cellular function of Btk, and thus, are valuable research tools for the identification of cell signalling proteins of therapeutic interest.

The present invention fulfills this need, and provides further related advantages.

SUMMARY

Inhibitors of kinase activity, which may generally be described as heterocyclic substituted imidazo[1,2-a]pyrazin-8-ylamines and related compounds, are disclosed herein. Certain compounds provided herein are highly active and/or specific inhibitors of Btk (Bruton's tyrosine kinase) activity.

One embodiment provides a compound of Formula I

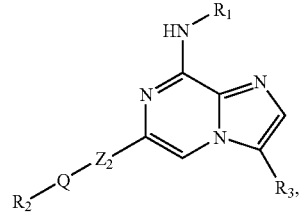

(Formula I)

and the pharmaceutically acceptable forms thereof.

Within Formula I $R_1$ is

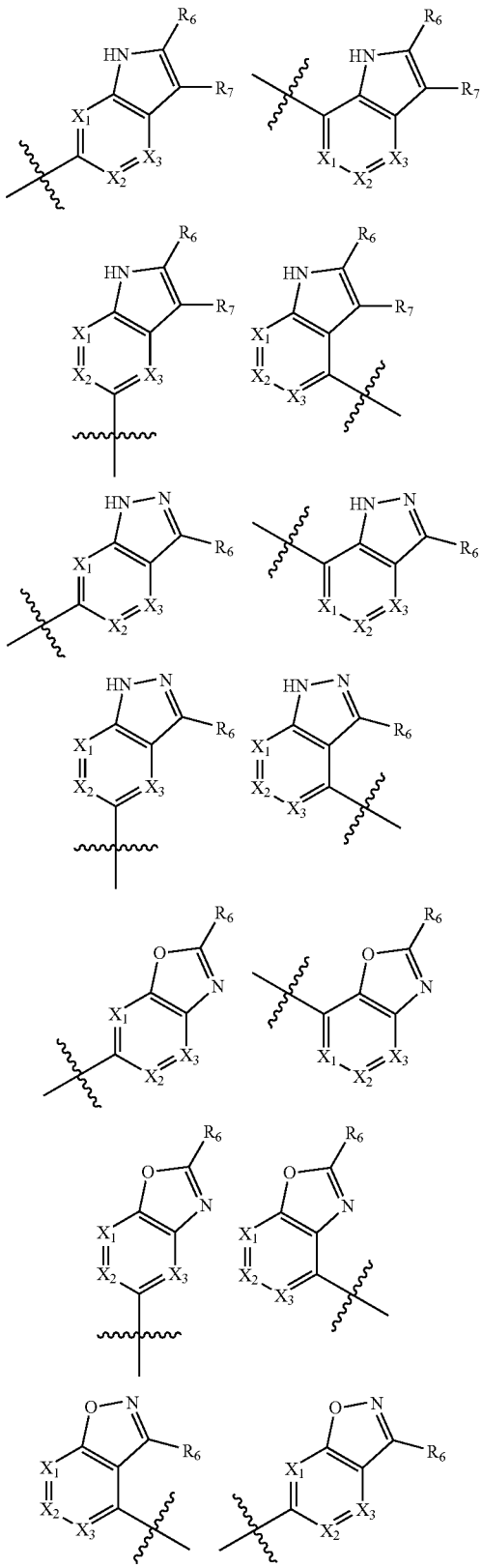

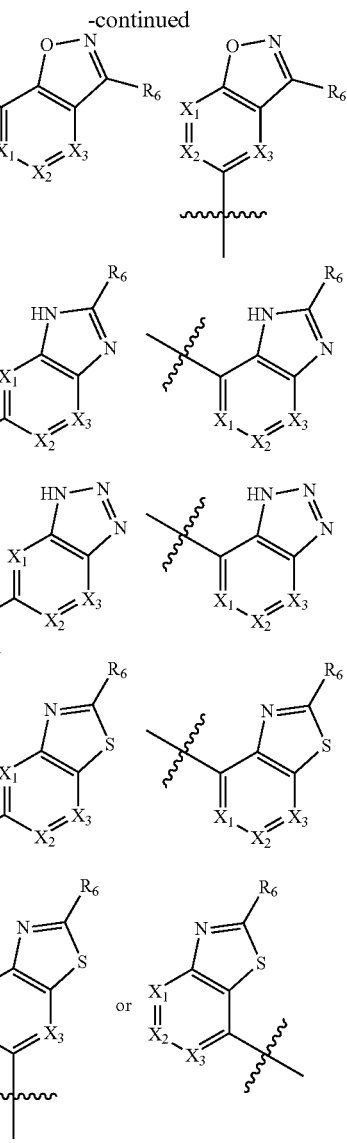

$X_1$ is N or CR; $X_2$ is N or CR; and $X_3$ is N or CR; wherein no more than one of $X_1$, $X_2$, and $X_3$ are N.

Each R is independently hydrogen, hydroxy, cyano, halogen, $C_1$-$C_2$alkyl, $C_1$-$C_2$alkoxy, $C_1$-$C_2$haloalkyl, or $C_1$-$C_2$haloalkoxy.

$Z_2$ is a divalent linking group selected from para-phenylene, meta-phenylene, ortho-phenylene, and naphthylene, each of which is substituted with one group $R_2$-Q-, where Q is

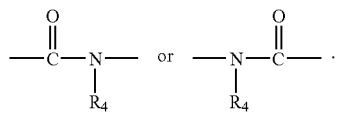

$R_4$ is hydrogen; $C_1$-$C_6$alkyl; or phenyl or heteroaryl wherein the phenyl or heteroaryl is substituted with 0 to 3 substituents independently chosen from hydroxy, nitro, cyano, amino, halogen, —CHO, —COOH, —$CONH_2$, $C_1$-$C_6$alkyl, $C_1$-$C_6$alkoxy, $C_1$-$C_6$haloalkyl, $C_1$-$C_6$haloalkoxy, ($C_1$-$C_6$alkoxy)$C_1$-$C_6$alkoxy, mono- and di-($C_1$-$C_6$alkyl)amino, amino$C_1$-$C_6$alkyl, $C_1$-$C_6$alkylthio, mono- and di-($C_1$-$C_6$alkyl)amino$C_1$-$C_6$alkyl, $C_3$-$C_7$cycloalkyl, $C_2$-$C_6$alkanoyl, $C_1$-$C_6$alkoxycarbonyl, heterocycloalkyl, amido, sulfonamide, $C_2$-$C_6$alkenyl, $C_2$-$C_6$alkynyl, and heteroaryl.

$R_2$ is either (a) or (b) as follows:

(a) $C_1$-$C_7$alkyl, $C_3$-$C_7$cycloalkyl, ($C_3$-$C_7$cycloalkyl)$C_1$-$C_7$alkyl, heterocycloalkyl, (heterocycloalkyl)$C_1$-$C_2$alkyl, $C_1$-$C_6$alkoxy, ($C_3$-$C_7$cycloalkyl)methyl, ($C_1$-$C_6$alkoxy), or ($C_1$-$C_6$alkoxy)$C_1$-$C_6$alkoxy, each of which is substituted with 0 to 3 substituents independently chosen from hydroxy, nitro, cyano, amino, halogen, —CHO, —COOH, —$CONH_2$, $C_1$-$C_6$alkyl, $C_1$-$C_6$alkoxy, $C_1$-$C_6$haloalkyl, $C_1$-$C_6$haloalkoxy, ($C_1$-$C_6$alkoxy)$C_1$-$C_6$alkoxy, mono- and di-($C_1$-$C_6$alkyl)amino, amino$C_1$-$C_6$alkyl, $C_1$-$C_6$alkylthio, mono- and di-($C_1$-$C_6$alkyl)amino$C_1$-$C_6$alkyl, $C_3$-$C_7$cycloalkyl, $C_2$-$C_6$alkanoyl, $C_1$-$C_6$alkoxycarbonyl, heterocycloalkyl, amido, sulfonamide, $C_2$-$C_6$alkenyl, $C_2$-$C_6$alkynyl, phenyl, and heteroaryl; or (b) phenyl or heteroaryl, each of which is substituted with 0 to 3 substituents independently chosen from hydroxy, nitro, cyano, amino, halogen, —CHO, —COOH, —$CONH_2$, $C_1$-$C_6$alkyl, $C_1$-$C_6$alkoxy, $C_1$-$C_6$haloalkyl, $C_1$-$C_6$haloalkoxy, ($C_1$-$C_6$alkoxy)$C_1$-$C_6$alkoxy, mono- and di-($C_1$-$C_6$alkyl)amino, amino$C_1$-$C_6$alkyl, $C_1$-$C_6$alkylthio, mono- and di-($C_1$-$C_6$alkyl)amino$C_1$-$C_6$alkyl, ($C_3$-$C_7$cycloalkyl)$C_0$-$C_2$alkyl, $C_2$-$C_6$alkanoyl, $C_1$-$C_6$alkoxycarbonyl, (heterocycloalkyl)$C_0$-$C_2$alkyl, amido, sulfonamide, $C_2$-$C_6$alkenyl, $C_2$-$C_6$alkynyl, and heteroaryl.

$R_3$ is hydrogen, $C_1$-$C_7$alkyl, heterocycloalkyl, or $C_3$-$C_7$cycloalkyl ring.

$R_6$ and $R_7$ are independently hydrogen, hydroxy, cyano, halogen, $C_1$-$C_2$alkyl, $C_1$-$C_2$alkoxy, $C_1$-$C_2$haloalkyl, or $C_1$-$C_2$haloalkoxy.

In certain embodiments compounds and forms thereof of Formula I, which exhibit an $IC_{50}$ of 1 micromolar or less, 100 nanomolar or less, or 10 nanomolar or less in standard biochemical assay for Btk activity, such as the biochemical assay described in Example 7, are provided herein. Preferred compounds described herein are highly active inhibitors of B-cell proliferation. For example certain compounds described herein exhibit an $IC_{50}$ value less than or equal to 10 micromolar, or an $IC_{50}$ value less than or equal to 1 micromolar, or an $IC_{50}$ value less than or equal to 500 nM in the tritiated thymidine incorporation assay for B-cell proliferation described in Example 9. Preferred compounds described herein are specific inhibitors of B-cell proliferation, exhibiting an $IC_{50}$ value that is at least 3-fold, preferably 5-fold, and more preferably 10-fold greater for T-cell proliferation than the $IC_{50}$ for B-cell proliferation. The $IC_{50}$ for T-cell proliferation may be determined via a standard assay for T-cell proliferation such as the thymidine incorporation assay of Example 10.

A method for determining the presence of Btk in a sample, comprising contacting the sample with a compound or form thereof of Formula I under conditions that permit detection of Btk activity, detecting a level of Btk activity in the sample, and there from determining the presence or absence of Btk in the sample, is also provided herein.

Pharmaceutical compositions, comprising one or more compounds of Formula I, or any pharmaceutically acceptable form thereof, together with at least one pharmaceutically acceptable carrier or excipient, are provided herein.

Other embodiments pertain to packaged pharmaceutical compositions which comprise a pharmaceutical composition, comprising one or more compounds of Formula I or any pharmaceutically acceptable form thereof, together with at least one pharmaceutically acceptable carrier or excipient in a container and optionally having instructions for using the pharmaceutical composition to treat a patient. Preferably the instructions are instructions for using the pharmaceutical composition to treat a patient suffering from a disease responsive to inhibition of Btk activity.

Still other embodiments pertain to a method of inhibiting Btk kinase. In certain embodiments the method comprises contacting a cell or cells expressing Btk, either in vivo or in vitro, with a compound of Formula I or form thereof in an amount sufficient to detectably inhibit Btk activity in vitro.

Inhibiting Btk activity can effectively inhibit B-cell proliferation. Btk inhibitors that are orally bioavailable, such as certain compounds and forms of Formula I, are particularly desirable for this purpose. Thus a method of inhibiting B-cell proliferation, by contacting cells expressing Btk, either in vivo or in vitro with a compound or form thereof of Formula I in an amount sufficient to detectably inhibit the activity of Btk in vitro is provided herein.

Methods for treating a patient having at least one disease responsive to inhibition of Btk activity and/or responsive to inhibition of B-cell proliferation, are provided herein. Such methods comprise administering to the patient an effective amount of a compound or form thereof of Formula I. The patient may be a mammal. Preferably the patient is a human patient, however methods of treating non-human patients are included herein. For example in some embodiments the patient is a companion animal, such as a cat or dog, or the patient is a livestock animal, such as a horse, cow, or pig. Particularly included herein are methods in which the disease responsive to Btk inhibition is cancer, an autoimmune and/or inflammatory disease, or an acute inflammatory reaction. Preferably the compound is also a specific inhibitor of B-cell proliferation, exhibiting an $IC_{50}$ value that is at least 3-fold, preferably 5-fold, and more preferably 10-fold greater for T-cell proliferation than the $IC_{50}$ value for B-cell proliferation.

Methods of treatment include administering a compound of Formula I as a single active agent or administering a compound of Formula I in combination with one or more other active agents.

DETAILED DESCRIPTION

Certain terms to be used herein are provided prior to setting forth the invention in detail. Compounds of the present invention are described using standard nomenclature. Unless defined otherwise, all technical and scientific terms used herein have the same meaning as is commonly understood by one of skill in the art to which this invention belongs.

Chemical Description and Terminology

Formula I includes all subformulae thereof. For example Formula I includes compounds of Formulas 1 to 7.

Certain compounds are described herein using a general formula that includes variables, e.g. $R_1$, $R_2$, $R_3$, $Q$, $X_1$, $X_2$, $X_3$, and $Z_2$. Unless otherwise specified, each variable within such a formula is defined independently of other variables. When any variable occurs more than one time in Formula I, its definition on each occurrence is independent of its definition at every other occurrence.

In accordance with the usual meaning of "a" and "the" in patents, reference to "a" kinase or "the" kinase is inclusive of one or more kinases. Unless otherwise specified the term "compounds" includes all pharmaceutically acceptable forms of the disclosed structures.

In certain situations, the compounds of Formula I may contain one or more asymmetric elements such as stereogenic centers, stereogenic axes and the like, e.g. asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In addition, compounds with carbon-carbon double bonds may occur in Z- and E-forms, with all isomeric forms of the compounds being included in the present invention. In these situations, the single enantiomers, i.e., optically active forms, can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column.

Where a compound exists in various tautomeric forms, the invention is not limited to any one of the specific tautomers, but rather includes all tautomeric forms.

The present invention is intended to include all isotopes of atoms occurring in the present compounds. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

The term "substituted", as used herein, means that any one or more hydrogens on the designated atom or group is replaced with a selection from the indicated group, provided that the designated atom's normal valence is not exceeded. When the substituent is oxo (i.e., =O), then 2 hydrogens on the atom are replaced. When aromatic moieties are substituted by an oxo group, the aromatic ring is replaced by the corresponding partially unsaturated ring. For example a pyridyl group substituted by oxo is a pyridone. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent.

Suitable groups that may be present on a "substituted" position include, but are not limited to, e.g., halogen; cyano; hydroxyl; nitro; azido; alkanoyl (such as a $C_2$-$C_6$alkanoyl group such as acyl or the like); carboxamido; alkyl groups (typically having 1 to about 8 carbon atoms, or 1 to about 6 carbon atoms); cycloalkyl groups, alkenyl and alkynyl groups (including groups having one or more unsaturated linkages and from 2 to about 8, or 2 to about 6 carbon atoms); alkoxy groups having one or more oxygen linkages and from 1 to about 8, or from 1 to about 6 carbon atoms; aryloxy such as phenoxy; alkythio groups including those having one or more thioether linkages and from 1 to about 8 carbon atoms, or from 1 to about 6 carbon atoms; alkylsulfinyl groups including those having one or more sulfinyl linkages and from 1 to about 8 carbon atoms, or from 1 to about 6 carbon atoms; alkylsulfonyl groups including those having one or more sulfonyl linkages and from 1 to about 8 carbon atoms, or from 1 to about 6 carbon atoms; aminoalkyl groups including groups having one or more N atoms and from 1 to about 8, or from 1 to about 6 carbon atoms; aryl having 6 or more carbons and one or more rings, (e.g., phenyl, biphenyl, naphthyl, or the like, each ring either substituted or unsubstituted aromatic); arylalkyl having 1 to 3 separate or fused rings and from 6 to about 18 ring carbon atoms, with benzyl being an exemplary arylalkyl group; arylalkoxy having 1 to 3 separate or fused rings and from 6 to about 18 ring carbon atoms, with benzyloxy being an exemplary arylalkoxy group; or a saturated, unsaturated, or aromatic heterocyclic group having 1 to 3 separate or fused rings with 3 to about 8 members per ring and one or more N, O, or S atoms, e.g. coumarinyl, quinolinyl, isoquinolinyl, quinazolinyl, pyridyl, pyrazinyl, pyrimidinyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such heterocyclic groups may be further substituted, e.g. with hydroxy, alkyl, alkoxy, halogen or amino.

A dash ("—") that is not between two letters or symbols is used to indicate a point of attachment for a substituent. For example, —CHO is attached through carbon of the carbonyl (C=O) group.

By "amido" is meant —NHC(O)R, wherein the R group can be a straight or branched chain $C_1$-$C_7$alkyl, in which the branched alkyl chains may form a 3-7 membered cycloalkyl ring, each of which may be unsubstituted or substituted with 1-3 halogen, $C_1$-$C_6$alkyl, $C_1$-$C_6$haloalkyl, $C_1$-$C_6$haloalkoxy, $C_1$-$C_6$alkoxy, mono- or di($C_1$-$C_6$alkyl)amino. "Amido" also includes —C(O)NR$_2$, wherein each R may independently be hydrogen, a straight or branched chain $C_1$-$C_7$alkyl, in which the branched alkyl chains may form a 3-7 membered cycloalkyl ring, the straight or branched chain alkyl may be unsubstituted or substituted with 1-3 substituents independently chosen from halogen, $C_1$-$C_6$alkyl, $C_1$-$C_6$haloalkyl, $C_1$-$C_6$haloalkoxy, $C_1$-$C_6$alkoxy, mono- and di($C_1$-$C_6$alkyl)amino.

By "alkyl" is meant a straight or branched chain alkyl group having the indicated number of carbon atoms. For example $C_1$-$C_6$alkyl is a straight or branched chain alkyl of from 1 to about 6 carbon atoms. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like.

By "C1-$C_n$alkoxy" is meant an alkyl group of the indicated number of carbon atoms, for example $C_1$-$C_6$alkoxy, attached through an oxygen bridge such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, 3-methylpentoxy, and the like. Preferred alkoxy groups herein are $C_1$-$C_4$alkoxy groups.

By "(C1-Cnalkoxy)C1-Cnalkoxy" is meant an alkoxy group as defined above attached through an oxygen atom to the alkyl group of a second alkoxy group, wherein the entire structure is attached through the second oxygen atom. Suitable examples include, but are not limited to, (ethoxy)ethoxy, (ethoxy)methoxy, methoxy(methoxy), and the like.

By "C1-Cn alkylthio" is meant an alkyl group of indicated number of carbon atoms attached through a sulfur bridge.

By "$C_2$-$C_n$alkanoyl" is meant an ester group of the formula —OC(O)($C_2$-$C_n$alkyl), for example —OC(O)(C2-Cnalkyl), attached through the ester oxygen. Conversely, by "C1-C6alkoxycarbonyl" is meant an ester group of the formula (C1-C6alkoxy)C(O)— attached through the carbonyl carbon.

By "C2-Cnalkenyl" is meant a straight or branched hydrocarbon chain having the indicated number of carbon atoms and comprising one or more unsaturated carbon-carbon double bonds, which may occur in any stable point along the chain. Examples of such groups include ethenyl and propenyl.

By "C2-Cnalkynyl" is meant a straight or branched hydrocarbon chain having the indicated number of carbon atoms and comprising one or more triple carbon-carbon bonds that may occur in any stable point along the chain, such as ethynyl and propynyl.

By "aminoalkyl" is meant an alkyl group as defined above, have the indicated number of carbon atoms, substituted with at least one amino substituent.

"C3-C7cycloalkyl" indicates saturated hydrocarbon ring groups, having the specified number of carbon atoms, usually from 3 to about 7 ring carbon atoms. Examples of cycloalkyl groups include cyclopropyl, cyclobutyl, cyclopentyl, or cyclohexyl as well as bridged or caged saturated ring groups such as norbornane.

By "(C3-C7cycloalkyl)C1-Cnalkyl" is meant C3-C7cycloalkyl as defined above linked through an alkyl group. Examples include (C3-C7cyclolakyl)methyl groups such as cyclopropylmethyl.

The term "halo" or "halogen" includes fluorine, chlorine, bromine, and iodine.

"C1-Cnhaloalkyl" indicates both branched and straight-chain saturated aliphatic hydrocarbon groups having the specified number of carbon atoms, substituted with 1 or more halogen atoms, generally up to the maximum allowable number of halogen atoms. Examples of haloalkyl include, but are not limited to, trifluoromethyl, difluoromethyl, 2-fluoroethyl, and penta-fluoroethyl.

"C1-Cnhaloalkoxy" indicates a haloalkyl group as defined above attached through an oxygen bridge.

By "heteroaryl" is meant a stable 5- to 7-membered monocyclic or 7- to 10-membered bicyclic heterocyclic ring which contains at least 1 aromatic ring that contains from 1 to 4, or preferably from 1 to 3, heteroatoms chosen from N, O, and S, with remaining ring atoms being carbon. When the total number of S and O atoms in the heteroaryl group exceeds 1, these heteroatoms are not adjacent to one another. It is preferred that the total number of S and O atoms in the heteroaryl group is not more than 2. It is particularly preferred that the total number of S and O atoms in the aromatic heterocycle is not more than 1. Examples of heteroaryl groups include, but are not limited to, systems (as numbered from the linkage position assigned priority 1), such as 2-pyridyl, 3-pyridyl, 4-pyridyl, 2,3-pyrazinyl, 3,4-pyrazinyl, 2,4-pyrimidinyl, 3,5-pyrimidinyl, 2,3-pyrazolinyl, 2,4-imidazolinyl, isoxazolinyl, oxazolinyl, thiazolinyl, thiadiazolinyl, tetrazolyl, thienyl, benzothiophenyl, furanyl, benzofuranyl, benzoimidazolinyl, indolinyl, pyridizinyl, triazolyl, quinolinyl, pyrazolyl, and 5,6,7,8-tetrahydroisoquinoline.

By "heterocycloalkyl" is meant a single aliphatic ring containing at least 2 carbon atoms in addition to 1 to about 3 heteroatoms independently selected from oxygen, sulfur, or nitrogen, as well as combinations comprising at least one of the foregoing heteroatoms. Suitable heterocycloalkyl groups include, for example (as numbered from the linkage position assigned priority 1), 2-pyrrolinyl, 2,3-pyrazolidinyl, 2-piperidyl, 3-piperidyl, 4-piperdyl, 2,5-piperzinyl, and pyrrolidinyl. Morpholinyl groups are also contemplated, including 2-morpholinyl and 3-morpholinyl (numbered wherein the oxygen is assigned priority 1) as well as 2- and 3-thiomorpholinyl.

By "(heterocycloalkyl)C1-C2alkyl" is meant a heterocycloalkyl as defined above linked through an alkyl bridge.

"Mono- and/or di-(C1-Cnalkyl)amino" indicates secondary or tertiary alkyl amino groups, wherein the alkyl groups are as defined above and have the indicated number of carbon atoms. The point of attachment of the alkylamino group is on the nitrogen. Examples of mono- and di-alkylamino groups include ethylamino, dimethylamino, and methyl-propyl-amino.

By "mono- and di-(C1-C6alkyl) aminoC1-C6alkyl" is meant mono- or di-(C1-C6alkyl)amino as defined above linked by a C1-C6alkyl bridge.

By "sulfonamide" is meant —S(O)2N— in either S-linked (wherein the nitrogen atom can be unsubstituted, or mono- or di-substituted with straight or branched chain C1-C7alkyl, in which the branched alkyl chains may form a 3-7 membered cycloalkyl) or N-linked orientation, wherein the sulfur atom can be unsubstituted or mono- or di-substituted with straight or branched chain C1-C7alkyl, in which the branched alkyl chains may form a 3-7 membered cycloalkyl ring, each of straight or branched chain alkyl substituent of a sulfonamide group may be unsubstituted or substituted with 1 to about 3 substituents independently chosen from halogen, C1-C6alkyl, C1-C6haloalkyl, C1-C6haloalkoxy, C1-C6alkoxy, mono- and di(C1-C6alkyl)amino.

"Pharmaceutically acceptable forms" of the compounds recited herein include pharmaceutically acceptable salts, hydrates, solvates, crystal forms, polymorphs, chelates, non-covalent complexes, esters, clathrates, prodrugs, and mixtures of such compounds. Pharmaceutically acceptable salts are a preferred pharmaceutically acceptable form.

"Pharmaceutically acceptable salts" include derivatives of the disclosed compounds wherein the parent compound is modified by making non-toxic acid or base salts thereof, and further refers to pharmaceutically acceptable solvates of such compounds and such salts. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—(CH2)n-COOH where n is 0-4, and the like. The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts may be found, e.g., in *Remington's Pharmaceutical Sciences,* 17th ed., Mack Publishing Company, Easton, Pa., p. 1418 (1985).

The term "prodrugs" includes any compounds that become compounds of Formula I when administered to a mammalian subject, e.g., upon metabolic processing of the prodrug. Examples of prodrugs include, but are not limited to, acetate, formate and benzoate and like derivatives of functional groups (such as alcohol or amine groups) in the compounds of Formula I.

The term "active agent" is used to indicate a compound, including any pharmaceutically form thereof, or natural product, which has biological activity. Preferably an "active agent" is a compound having pharmaceutical utility. For example an active agent may be a compound of Formula I, or an anti-cancer or anti-inflammatory therapeutic, which is not a compound of Formula I.

The term "effective amount" of a compound of this invention means an amount effective, when administered to a human or non-human patient, to provide a therapeutic benefit such as amelioration of symptoms, slowing of disease progression, or prevention of disease e.g., an effective amount may be an amount sufficient to decrease the symptoms of a disease responsive to Btk inhibition, and preferably is an amount sufficient to reduce cancer symptoms, the symptoms of an autoimmune and/or inflammatory disease, or the symptoms of an acute inflammatory reaction. In some embodiments an effective amount of a compound described herein is an amount sufficient to decrease the number of detectable cancerous cells in an organism, detectably slow or stop the growth of a cancerous tumor, or more preferably an amount sufficient to shrink a cancerous tumor. In certain circumstances a patient suffering from cancer may not present symptoms of being affected. Thus, a therapeutically effective amount of a compound is also an amount sufficient to prevent a significant increase or significantly reduce the detectable level of cancerous cells or cancer markers in the patient's blood, serum, or tissues. In methods described herein for treating autoimmune and/or inflammatory diseases or acute inflammatory reactions, an effective amount may also be an amount sufficient, when administered to a patient, to detectably slow progression of the disease, or prevent the patient to whom the compound is given from presenting symptoms of the autoimmune and/or inflammatory disease, or acute inflammatory response. In certain methods described herein for treating autoimmune and/or inflammatory diseases or acute inflammatory reactions, an effective amount may also be an amount sufficient to produce a detectable decrease in the amount of a marker protein or cell type in the patient's blood or serum. For example, in some embodiments an effective amount is an amount of a compound described herein sufficient to significantly decrease the number of B-cells. In another example, in some embodiments an effective amount is an amount of a compound described herein sufficient to decrease the level of anti-acetylcholine receptor antibody in a the blood of a patient with the disease myasthenia gravis, The term "inhibition" indicates a significant decrease in the baseline activity of a biological activity or process. "Inhibition of Btk activity" refers to a decrease in Btk activity as a direct or indirect response to the presence of a compound of Formula I, relative to the activity of Btk in the absence of the compound. The decrease in activity may be due to the direct interaction of the compound with Btk, or due to the interaction of the compound with one or more other factors that in turn affect Btk activity. For example, the presence of the compound may decrease Btk activity by directly binding to the Btk, by causing (directly or indirectly) another factor to decrease Btk activity, or by (directly or indirectly) decreasing the amount of Btk present in the cell or organism.

Inhibition of Btk activity also refers to observable inhibition of Btk activity in a standard biochemical assay for Btk activity, such as the ATP hydrolysis assay of Example 7. Preferred inhibitors of Btk activity have an $IC_{50}$ value less than or equal to 1 micromolar, more preferably less than or equal to less than 100 nanomolar, and still more preferably less than or equal to 10 nanomolar.

Without wishing to be bound to any particular theory it is believed that the inhibition of Btk activity causes an inhibition of B-cell proliferation. "Inhibition of B-cell proliferation" refers to inhibition of proliferation of abnormal B-cells, such as cancerous B-cells, e.g. lymphoma B-cells and/or inhibition of normal, non-diseased B-cells. The term "inhibition of B-cell proliferation" indicates any significant decrease in the number of B-cells, either in vitro or in vivo. Thus in vitro an inhibition of B-cell proliferation would be any significant decrease in the number of B-cells in an in vitro sample contacted with a compound of Formula I as compared to a matched sample not contacted with a compound of Formula I.

Inhibition of B-cell proliferation also refers to observable inhibition of B-cell proliferation in a standard thymidine incorporation assay for B-cell proliferation, such as the assay of Example 9. Preferred inhibitors of B-cell proliferation have an $IC_{50}$ value less than or equal to 10 micromolar, more preferably less than or equal to less than 1 micromolar, and still more preferably less than or equal to 500 nanomolar.

By "significant" is meant any detectable change that is statistically significant in a standard parametric test of statistical significance such as Student's T-test, where $p<0.05$.

A "disease responsive to Btk inhibition" is a disease in which inhibiting Btk kinase provides a therapeutic benefit such as an amelioration of symptoms, decrease in disease progression, prevention or delay of disease onset, or inhibition of aberrant activity of certain cell-types (monocytes, B-cells, and mast cells).

Heterocyclic Substituted Imidazo[1,2-a]pyrazine Compounds

In addition to compounds of Formula I (above),

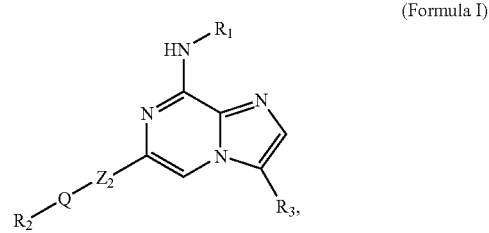

(Formula I)

and the pharmaceutically acceptable forms thereof, wherein variables $R_1$, $R_2$, $R_3$, Q, and $R_2$ carry the definitions set forth above compounds and forms thereof in which one or more of the following conditions is met are also provided:

(i) $Z_2$ is meta-phenylene.
(ii) $X_1$, $X_2$, and $X_3$ are all CR.
(iii) $X_1$ is N, and $X_2$ and $X_3$ are both CR.
(iv) $X_1$ and $X_3$ are both CR and $X_2$ is N.
(v) $X_1$ and $X_2$ are both CR and $X_3$ is N.
(vi) Each R is independently hydrogen, halogen, methyl, or methoxy.
(vii) $R_2$ is phenyl or heteroaryl, each of which is substituted with 0 to 3 substituents independently chosen from hydroxy, nitro, cyano, amino, halogen, —CHO, —COOH, —CONH$_2$, $C_1$-$C_6$alkyl, $C_1$-$C_6$alkoxy, $C_1$-$C_6$haloalkyl, $C_1$-$C_6$haloalkoxy, ($C_1$-$C_6$alkoxy)$C_1$-$C_6$alkoxy, mono- and di-($C_1$-$C_6$alkyl)amino, amino$C_1$-$C_6$alkyl, $C_1$-$C_6$alkylthio, mono- and di-($C_1$-$C_6$alkyl) amino$C_1$-$C_6$alkyl, ($C_3$-$C_7$cycloalkyl)$C_0$-$C_2$alkyl, $C_2-C_6$alkanoyl, $C_1-C_6$alkoxycarbonyl, (heterocycloalkyl)$C_0-C_2$alkyl, amido, sulfonamide, $C_2-C_6$alkenyl, $C_2-C_6$alkynyl, and heteroaryl.

(viii) $R_2$ is phenyl or pyridyl, each of which is substituted with 1 to 3 substituents independently chosen from hydroxy, nitro, cyano, amino, halogen, —CHO, —COOH, —CONH$_2$, $C_1-C_6$alkyl, $C_1-C_6$alkoxy, $C_1-C_2$haloalkyl, $C_1-C_2$haloalkoxy, ($C_1-C_6$alkoxy)$C_1$-$C_6$alkoxy, mono- and di-($C_1-C_6$alkyl)amino, amino$C_1$-$C_6$alkyl, $C_1-C_6$alkylthio, mono- and di-($C_1-C_6$alkyl) amino$C_1-C_6$alkyl, ($C_3-C_7$cycloalkyl)$C_0-C_2$alkyl, $C_2-C_6$alkanoyl, $C_1-C_6$alkoxycarbonyl, (heterocycloalkyl)$C_0-C_2$alkyl, amido, and sulfonamide.

(ix) $R_2$ is phenyl or pyridyl, each of which is substituted with 1 to 3 substituents independently chosen from hydroxy, cyano, nitro, halogen, $C_1-C_2$alkyl, $C_1-C_2$alkoxy, $C_1-C_2$haloalkyl, $C_3-C_7$cycloalkyl, ($C_3$-$C_7$cycloalkyl)methyl, heterocycloalkyl, (heterocycloalkyl)methyl, and $C_1-C_2$haloalkoxy.

(x) $R_2$ is phenyl or pyridyl, each of which is substituted with 1 to 3 substituents independently chosen from cyano, nitro, halogen, methyl, methoxy, trifluoromethyl, and trifluoromethoxy.

(xi) $R_2$ is phenyl or pyridyl, each of which is unsubstituted.

(xii) $R_4$ is hydrogen or methyl.

(xiii) $R_3$ is hydrogen or $C_1-C_4$alkyl.

(xiv) $R_3$ is hydrogen.

(xv) $R_6$ and $R_7$ are each independently hydrogen, halogen, cyano, $C_1-C_2$alkyl, $C_1-C_2$alkoxy, trifluoromethyl, or trifluoromethoxy.

(xvi) $R_1$ is

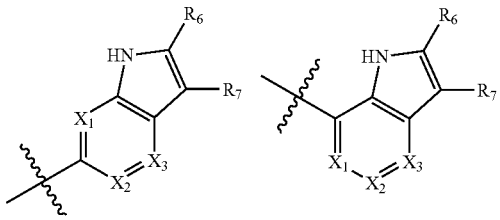

(xvii) $R_1$ is

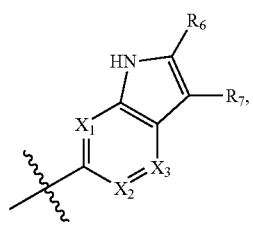

i.e. a compound or form thereof of Formula 2 is provided herein:

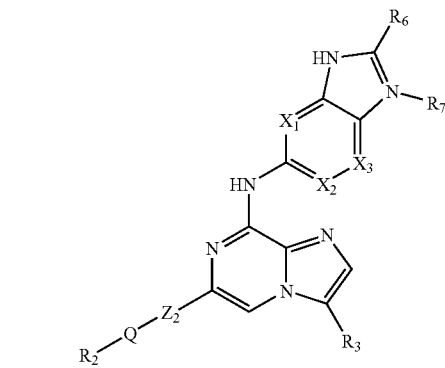

Formula 2

(xviii) $R_1$ is

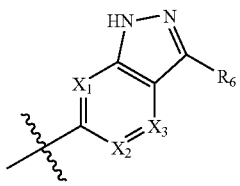 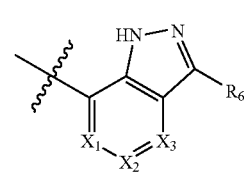

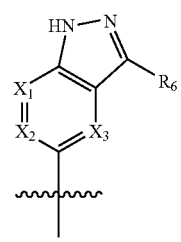 or 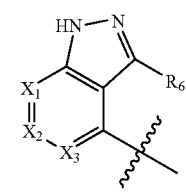

(xix) $R_1$ is

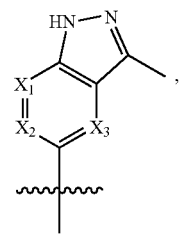

i.e. a compound or form thereof of Formula 3 is provided herein:

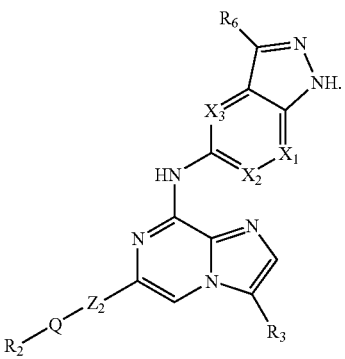

Formula 3

(xx) $R_1$ is

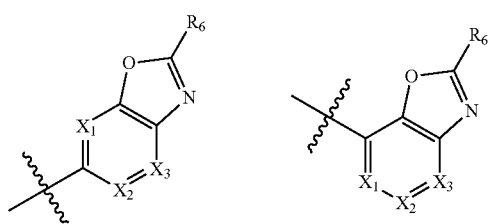
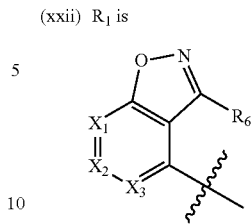
(xxi) R₁ is
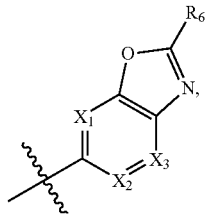
i.e. a compound or form thereof of Formula 4 is provided herein:
Formula 4
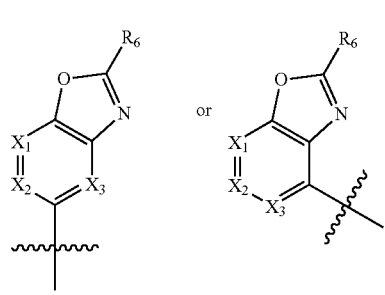
(xxii) R₁ is
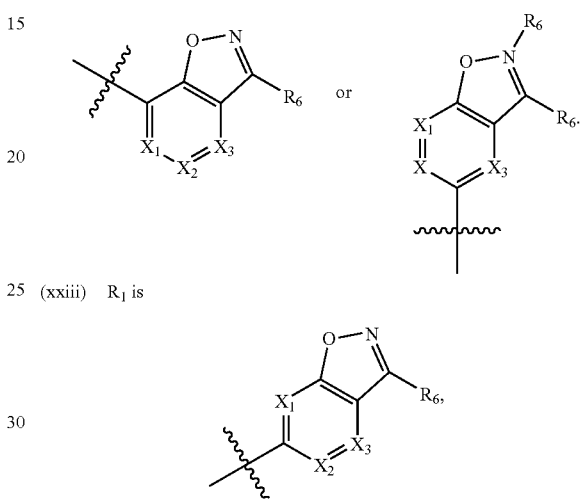
(xxiii) R₁ is
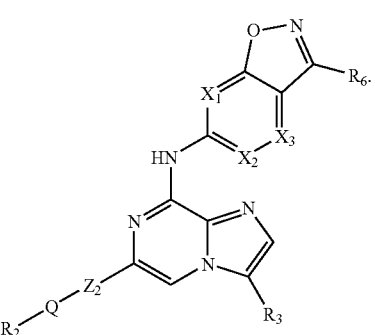
i.e. a compound or form thereof of Formula 5 is provided herein:
Formula 5
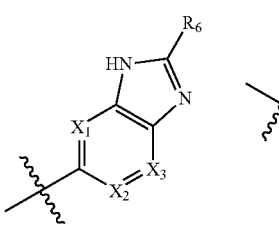
(xxiv) R₁ is
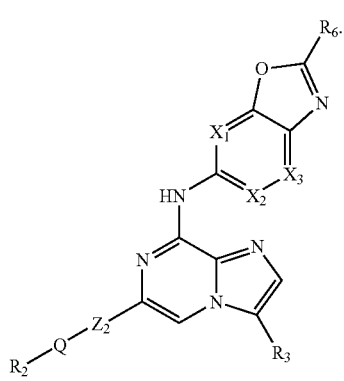
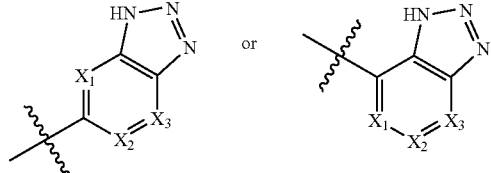

-continued (xxv) R₁ is

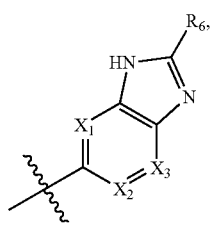

i.e. a compound or form thereof of Formula 6 is provided herein:

Formula 6

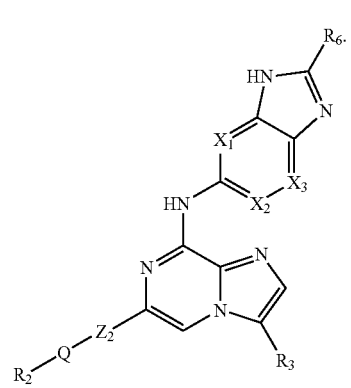

(xxvi) R₁ is

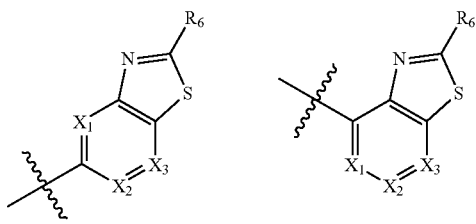

or

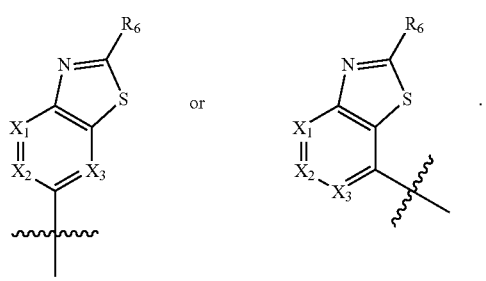

-continued (xxvii) R₁ is

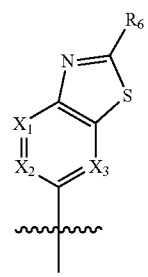

i.e. a compound or form thereof of Formula 7 is provided herein:

Formula 7

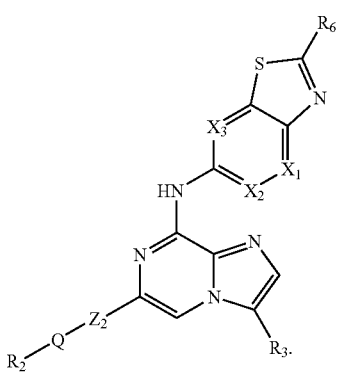

Compounds and forms thereof of Formula 2 to 7 wherein $X_1$, $X_2$, and $X_3$ are all CR are provided herein. Compounds and forms thereof of Formula 2 to 7 wherein X1, X2, and X3 are all CH are also provided herein.

The variables X1-X3, R1-R3, and Q, may carry any combination of definitions set forth above for these variables, so long as the combination results in a stable compound of Formula I. For example, a compound or form thereof of Formula I in which condition (xii) $R_4$ and $R_5$ are independently hydrogen or methyl and condition (xiii) $R_3$ is hydrogen or $C_1$-$C_4$alkyl, is provided herein.

Pharmaceutical Preparations

Compounds, salts, and any other pharmaceutically acceptable forms of the invention can be administered as the neat chemical, but are preferably administered as a pharmaceutical composition or formulation. Accordingly, the invention provides pharmaceutical formulations comprising a compound or pharmaceutically acceptable form of Formula I, together with one or more pharmaceutically acceptable carriers, excipients, adjuvants, diluents, or other ingredients.

Pharmaceutical carriers must be of sufficiently high purity and sufficiently low toxicity to render them suitable for administration to the animal being treated. The carrier can be inert or it can possess pharmaceutical benefits. The amount of carrier employed in conjunction with the compound is sufficient to provide a practical quantity of material for administration per unit dose of the compound.

Exemplary pharmaceutically acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; synthetic oils; vegetable oils, such as peanut oil, cottonseed oil, sesame oil, olive oil, and corn oil; polyols such as propylene glycol, glycerine, sorbitol, mannitol, and polyethylene glycol; alginic acid; phosphate buffer solutions; emulsifiers, such as the TWEENS; wetting agents, such sodium lauryl sulfate; coloring agents; flavoring agents; tableting agents; stabilizers; antioxidants; preservatives; pyrogen-free water; isotonic saline; and phosphate buffer solutions.

Optional active agents may be included in a pharmaceutical composition, which do not substantially interfere with the activity of the compound of the present invention.

Effective concentrations of one or more of the compounds of the invention including pharmaceutically acceptable salts, esters or other derivatives thereof are mixed with a suitable pharmaceutical carrier, excipients, adjuvant, or vehicle. In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN, or dissolution in aqueous sodium bicarbonate. Derivatives of the compounds, such as salts of the compounds or prodrugs of the compounds may also be used in formulating effective pharmaceutical compositions.

Upon mixing or addition of the compound(s) of the invention, the resulting mixture may be a solution, suspension, emulsion or the like. The form of the resulting mixture depends upon a number of factors, including the intended mode of administration and the solubility of the compound in the chosen carrier or vehicle. The effective concentration sufficient for ameliorating the symptoms of the disease treated and may be empirically determined.

Compounds of provided herein may be administered orally, topically, parenterally, intravenously, by intramuscular injection, by inhalation or spray, sublingually, transdermally, via buccal administration, rectally, as an ophthalmic solution, or by other means, in dosage unit formulations.

Dosage formulations suitable for oral use, include, for example, tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents, such as sweetening agents, flavoring agents, coloring agents and preserving agents, in order to provide pharmaceutically elegant and palatable preparations. Oral formulations contain between 0.1 and 99% of a compound of the invention and usually at least about 5% (weight %) of a compound of the present invention. Some embodiments contain from about 25% to about 50% or from 5% to 75% of a compound of invention.

Orally administered compositions also include liquid solutions, emulsions, suspensions, powders, granules, elixirs, tinctures, syrups, and the like. The pharmaceutically acceptable carriers suitable for preparation of such compositions are well known in the art. Oral formulations may contain preservatives, flavoring agents, sweetening agents, such as sucrose or saccharin, taste-masking agents, and coloring agents.

Typical components of carriers for syrups, elixirs, emulsions and suspensions include ethanol, glycerol, propylene glycol, polyethylene glycol, liquid sucrose, sorbitol and water. Syrups and elixirs may be formulated with sweetening agents, for example glycerol, propylene glycol, sorbitol or sucrose. Such formulations may also contain a demulcent.

Orally Administered Liquids Formulations

Compounds of the invention can be incorporated into oral liquid preparations such as aqueous or oily suspensions, solutions, emulsions, syrups, or elixirs, for example. Moreover, formulations containing these compounds can be presented as a dry product for constitution with water or other suitable vehicle before use. Such liquid preparations can contain conventional additives, such as suspending agents (e.g., sorbitol syrup, methyl cellulose, glucose/sugar, syrup, gelatin, hydroxyethyl cellulose, carboxymethyl cellulose, aluminum stearate gel, and hydrogenated edible fats), emulsifying agents (e.g., lecithin, sorbitan monsoleate, or acacia), non-aqueous vehicles, which can include edible oils (e.g., almond oil, fractionated coconut oil, silyl esters, propylene glycol and ethyl alcohol), and preservatives (e.g., methyl or propyl p-hydroxybenzoate and sorbic acid).

Suspensions

For a suspension, typical suspending agents include methylcellulose, sodium carboxymethyl cellulose, Avicel RC-591, tragacanth and sodium alginate; typical wetting agents include lecithin and polysorbate 80; and typical preservatives include methyl paraben and sodium benzoate.

Aqueous suspensions contain the active material(s) in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents; may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol substitute, or condensation products of ethylene oxide with partial esters derived from fatty acids and hexitol anhydrides, for example polyethylene sorbitan substitute. The aqueous suspensions may also contain one or more preservatives, for example ethyl, or n-propyl p-hydroxybenzoate.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Emulsions

Pharmaceutical compositions of the invention may also be in the form of oil-in-water emulsions. The oily phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate.

Dispersible Powders

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

Tablets and Capsules

Tablets typically comprise conventional pharmaceutically compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules (including time release and sustained release formulations) typically comprise one or more solid diluents disclosed above. The selection of carrier components often depends on secondary considerations like taste, cost, and shelf stability.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methylcellulose phthalate, ethyl cellulose, Eudragit coatings, waxes and shellac.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Injectable and Parenteral Formulations

Pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid are useful in the preparation of injectables.

Compounds of the invention may be administered parenterally in a sterile medium. Parenteral administration includes subcutaneous injections, intravenous, intramuscular, intrathecal injection or infusion techniques. The compound or compounds of the invention, depending on the vehicle and concentration used, can either be suspended or dissolved in the vehicle. Advantageously, adjuvants such as local anesthetics, preservatives and buffering agents can be dissolved in the vehicle. In many compositions for parenteral administration the carrier comprises at least about 90% by weight of the total composition. Preferred carriers for parenteral administration include propylene glycol, ethyl oleate, pyrrolidone, ethanol, and sesame oil.

Suppositories

Compounds of the invention may also be administered in the form of suppositories for rectal administration of the drug. These compositions can be prepared by mixing the drug with a suitable non-irritating excipient that is solid at ordinary temperatures but liquid at rectal temperature and will therefore melt in the rectum to release the drug. Such materials include cocoa butter and polyethylene glycols.

Topical Formulations

Compounds of the invention may be formulated for local or topical application, such as for topical application to the skin and mucous membranes, such as in the eye, in the form of gels, creams, and lotions and for application to the eye. Topical compositions of the present invention may be in any form including, for example, solutions, creams, ointments, gels, lotions, milks, cleansers, moisturizers, sprays, skin patches, and the like.

Such solutions may be formulated as 0.01%-10% isotonic solutions, pH about 5-7, with appropriate salts. Compounds of the invention may also be formulated for transdermal administration as a transdermal patch.

Topical compositions containing the active compound can be admixed with a variety of carrier materials well known in the art, such as, for example, water, alcohols, aloe vera gel, allantoin, glycerine, vitamin A and E oils, mineral oil, propylene glycol, PPG-2 myristyl propionate, and the like.

Other materials suitable for use in topical carriers include, for example, emollients, solvents, humectants, thickeners and powders. Examples of each of these types of materials, which can be used singly or as mixtures of one or more materials, are as follows:

Emollients, such as stearyl alcohol, glyceryl monoricinoleate, glyceryl monostearate, propane-1,2-diol, butane-1,3-diol, mink oil, cetyl alcohol, iso-propyl isostearate, stearic acid, iso-butyl palmitate, isocetyl stearate, oleyl alcohol, iso-propyl laurate, hexyl laurate, decyl oleate, octadecan-2-ol, isocetyl alcohol, cetyl palmitate, dimethylpolysiloxane, di-n-butyl sebacate, iso-propyl myristate, iso-propyl palmitate, iso-propyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, and myristyl myristate; propellants, such as propane, butane, iso-butane, dimethyl ether, carbon dioxide, and nitrous oxide; solvents, such as ethyl alcohol, methylene chloride, iso-propanol, castor oil, ethylene glycol monoethyl ether, diethylene glycol monobutyl ether, diethylene glycol monoethyl ether, dimethyl sulphoxide, dimethyl formamide, tetrahydrofuran; humectants, such as glycerin, sorbitol, sodium 2-pyrrolidone-5-carboxylate, soluble collagen, dibutyl phthalate, and gelatin; and powders, such as chalk, talc, fullers earth, kaolin, starch, gums, colloidal silicon dioxide, sodium polyacrylate, tetra alkyl ammonium smectites, trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, and ethylene glycol monostearate.

Compounds of the invention may also be topically administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Other Formulations

Other compositions useful for attaining systemic delivery of the subject compounds include sublingual, buccal and nasal dosage forms. Such compositions typically comprise one or more of soluble filler substances such as sucrose, sorbitol and mannitol, and binders such as acacia, microcrystalline cellulose, carboxymethyl cellulose, and hydroxypropyl methylcellulose. Glidants, lubricants, sweeteners, colorants, antioxidants and flavoring agents disclosed above may also be included.

Compositions for inhalation typically can be provided in the form of a solution, suspension or emulsion that can be administered as a dry powder or in the form of an aerosol using a conventional propellant (e.g., dichlorodifluoromethane or trichlorofluoromethane).

Additional Components

The compositions of the present invention may also optionally comprise an activity enhancer. The activity enhancer can be chosen from a wide variety of molecules that function in different ways to enhance therapeutic effects of compounds of the invention. Particular classes of activity enhancers include skin penetration enhancers and absorption enhancers.

Pharmaceutical compositions of the invention may also contain additional active agents can be chosen from a wide variety of molecules, which can function in different ways to enhance the therapeutic effects of a compound of the invention. These optional other active agents, when present, are typically employed in the compositions of the invention at a level ranging from about 0.01% to about 15%. Some embodiments contain from about 0.1% to about 10% by weight of the composition. Other embodiments contain from about 0.5% to about 5% by weight of the composition.

Packaged Formulations

The invention includes packaged pharmaceutical formulations. Such packaged formulations include a pharmaceutical composition containing one or more compounds, salts, or other pharmaceutically acceptable forms thereof, of the invention in a container and instructions for using the composition to treat a mammal (typically a human patient). Preferably the instructions are for using the pharmaceutical composition to treat a patient suffering from a disease responsive to inhibition of Btk activity and/or inhibition of B-cell proliferation. The invention includes providing prescribing information; for example, to a patient or health care provider, or as a label in a packaged pharmaceutical formulation. Prescribing information may include for example efficacy, dosage and administration, contraindication and adverse reaction information pertaining to the pharmaceutical formulation.

In all of the foregoing the compounds of the invention can be administered alone, as mixtures, or in combination with other active agents.

Methods of Treatment

Heterocyclic substituted imidazo[1,2-a]pyrazines active as kinase inhibitors, in particular Btk inhibitors are described herein. These inhibitors are useful for treating diseases responsive to kinase inhibition, including diseases responsive to Btk inhibition and/or inhibition of B-cell proliferation, in mammals. Without wishing to be bound to any particular theory, it is believed that the interaction of the compounds of Formula I with Btk results in the inhibition of Btk activity and thus in the pharmaceutical utility of these compounds. Other kinases that may be affected in addition to Btk include, but are not limited to, other tyrosine kinases and serine/threonine kinases.

Accordingly, the invention includes a method of treating a mammal, preferably a human patient, having a disease responsive to inhibition of Btk activity, comprising administrating to the mammal having such a disease, an effective amount of a compound of Formula I.

To the extent that Btk is implicated in any of the following, alleviation of the disease, disease symptoms, preventative, and prophylactic treatment is within the scope of this invention. In addition, as noted above, the compounds of Formula I may also inhibit other kinases, such that alleviation of disease, disease symptoms, preventative, and prophylactic treatment of conditions associated with these kinases is also within the scope of this invention.

Methods of treatment also include inhibiting Btk activity and/or inhibiting B-cell proliferation, by inhibiting ATP binding or hydrolysis by Btk or by some other mechanism, in vivo, in a patient suffering from a disease responsive to inhibition of Btk activity, by administering an effective concentration of a compound of Formula I to inhibit Btk activity in vitro. An effective concentration may be ascertained experimentally, for example by assaying blood concentration of the compound, or theoretically, by calculating bioavailability.

Diseases Responsive to Kinase Inhibition

Certain compounds described herein are useful for treating a patient suffering from a disease responsive to kinase inhibition.

Protein kinases, the largest family of human enzymes, are now considered to be the largest druggable target class. Encompassing well over 500 proteins (2% of the human genome), kinases play critical roles in signaling pathways controlling fundamental cellular processes such as proliferation, differentiation, and death (apoptosis). Abnormal kinase activity has been implicated in a wide range of diseases, including multiple cancers, autoimmune and/or inflammatory diseases, and acute inflammatory reactions. The multifaceted role of kinases in key cell signaling pathways provides a significant opportunity to identify novel drugs targeting kinases and signaling pathways.

Diseases Responsive to Btk Inhibition

The invention includes a method of treating a patient having cancer, an autoimmune and/or inflammatory disease, or an acute inflammatory reaction, by administering an effective amount of a compound of Formula I.

In a preferred embodiment, the condition responsive to inhibition of Btk activity and/or B-cell proliferation is cancer, an autoimmune and/or inflammatory disease, or an acute inflammatory reaction.

Preferably, the conditions and diseases that can be affected using compounds and compositions according to the invention include, but are not limited to:

autoimmune and/or inflammatory diseases, including but not limited to psoriasis, allergy, Crohn's disease, irritable bowel syndrome, Sjogren's disease, tissue graft rejection, and hyperacute rejection of transplanted organs, asthma, systemic lupus erythematosus (and associated glomerulonephritis), dermatomyositis, multiple sclerosis, scleroderma, vasculitis (ANCA-associated and other vasculitides), autoimmune hemolytic and thrombocytopenic states, Goodpasture's syndrome (and associated glomerulonephritis and pulmonary hemorrhage), atherosclerosis, rheumatoid arthritis, chronic idiopathic thrombocytopenic purpura (ITP), Addison's disease, Parkinson's disease, Alzheimer's disease, diabetes, septic shock, myasthenia gravis, and the like, acute inflammatory reactions, including but not limited to skin sunburn, inflammatory pelvic disease, inflammatory bowel disease, urethritis, uveitis, sinusitis, pneumonitis, encephalitis, meningitis, myocarditis, nephritis, osteomyelitis, myositis, hepatitis, gastritis, enteritis, dermatitis, gingivitis, appendicitis, pancreatitis, and cholocystitis, and cancer, including but not limited to, B-cell lymphoma, lymphoma (including Hodgkin's and non-Hodgkins lymphoma), hairy cell leukemia, multiple myeloma, chronic and acute myelogenous leukemia, and chronic and acute lymphocytic leukemia.

Btk is a known inhibitor of apoptosis in lymphoma B-cells. Defective apoptosis contributes to the pathogenesis and drug resistance of human leukemias and lymphomas. Thus, a method of promoting or inducing apoptosis in cells expressing Btk comprising contacting the cell with an agent that inhibits Btk activity is also provided herein.

Combination Therapy

The invention provides methods of treatment in which a compound of the invention is the only active agent given to a patient and also includes methods of treatment in which a compound of Formula I is given to a patient in combination with one or more additional active agent. Thus in one embodiment the invention provides a method of treating cancer, an autoimmune and/or inflammatory disease, or an acute inflammatory reaction, which comprises administering to a mammal in need thereof an effective amount of a compound of Formula I together with a second active agent, which is useful for treating an cancer, an autoimmune and/or inflammatory disease, or an acute inflammatory reaction. For example the second agent may be an anti-inflammatory agent. Treatment with the second active agent may be prior to, concomitant with, or following treatment with a compound of Formula I. In certain embodiments a compound of Formula I is combined with another active agent in a single dosage form. Suitable antitumor therapeutics that may be used in combination with a compound of Formula I include, but are not limited to chemotherapeutic agents, for example mitomycin C, carboplatin, taxol, cisplatin, paclitaxel, etoposide, doxorubicin, or a combination comprising at least one of the foregoing chemotherapeutic agents. Radiotherapeutic antitumor agents may also be used, alone or in combination with chemotherapeutic agents.

Btk inhibitors are useful as chemosensitizing agents, and, thus, are useful in combination with other chemotherapeutic drugs, in particular, drugs that induce apoptosis.

A method for increasing sensitivity of cancer cells to chemotherapy, comprising administering to a patient undergoing chemotherapy a chemotherapeutic agent together with a Btk inhibitor in an amount sufficient to increase the sensitivity of cancer cells to the chemotherapeutic agent is also provided herein.

Examples of other chemotherapeutic drugs that can be used in combination with Btk inhibitors include topoisomerase I inhibitors (camptothesin or topotecan), topoisomerase II inhibitors (e.g. daunomycin and etoposide), alkylating agents (e.g. cyclophosphamide, melphalan and BCNU), tubulin directed agents (e.g. taxol and vinblastine), and biological agents (e.g. antibodies such as anti CD20 antibody, IDEC 8, immunotoxins, and cytokines).

Included herein are methods of treatment in which a compound of Formula I is administered in combination with an anti-inflammatory agent. Anti-inflammatory agents include but are not limited to NSAIDs, non-specific and COX-2 specific cyclooxgenase enzyme inhibitors, gold compounds, corticosteroids, methotrexate, tumor necrosis factor (TNTF) antagonists, immunosuppressants and methotrexate.

Examples of NSAIDs include, but are not limited to ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors (i.e., a compound that inhibits COX-2 with an $IC_{50}$ that is at least 50-fold lower than the $IC_{50}$ for COX-1) such as celecoxib, valdecoxib, lumiracoxib, etoricoxib and/or rofecoxib.

In a further embodiment, the anti-inflammatory agent is a salicylate. Salicylates include by are not limited to acetylsalicylic acid or aspirin, sodium salicylate, and choline and magnesium salicylates.

The anti-inflammatory agent may also be a corticosteroid. For example, the corticosteroid may be cortisone, dexamethasone, methylprednisolone, prednisolone, prednisolone sodium phosphate, and prednisone.

In additional embodiments the anti-inflammatory agent is therapeutic agent is a gold compound such as gold sodium thiomalate or auranofin.

The invention also includes embodiments in which the anti-inflammatory agent is a metabolic inhibitor such as a dihydrofolate reductase inhibitor, such as methotrexate or a dihydroorotate dehydrogenase inhibitor, such as leflunomide.

Other embodiments of the invention pertain to combinations in which at least one anti-inflammatory compound is an anti-C5 monoclonal antibody (such as eculizumab or pexelizumab), a TNF antagonist, such as entanercept, or infliximab, which is an anti-TNF alpha monoclonal antibody.

Still other embodiments of the invention pertain to combinations in which at least one active agent is an immunosuppressant compound such as methotrexate, leflunomide, cyclosporine, tacrolimus, azathioprine, or mycophenolate mofetil.

Dosage Levels

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

Frequency of dosage may also vary depending on the compound used and the particular disease treated. However, for treatment of most autoimmune and/or inflammatory, a dosage regimen of 4 times daily or less is preferred and a dosage regimen of 1 or 2 times daily is particularly preferred.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease in the patient undergoing therapy.

EXAMPLES

Scheme 1

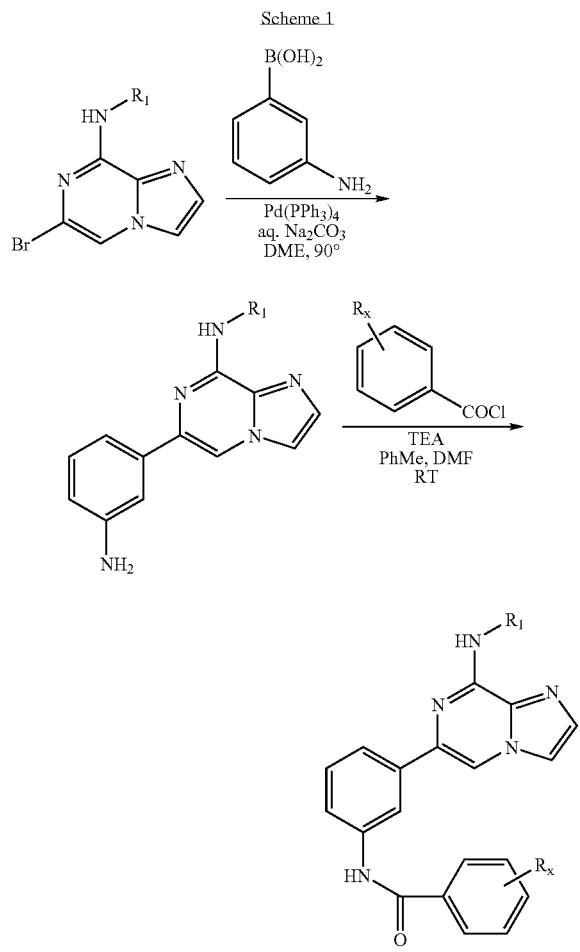

Scheme II

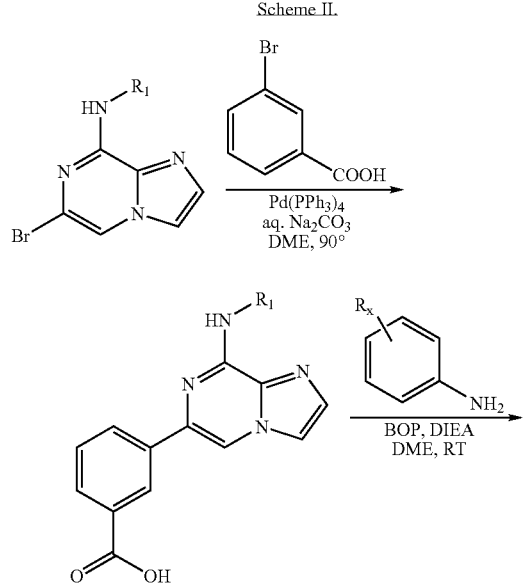

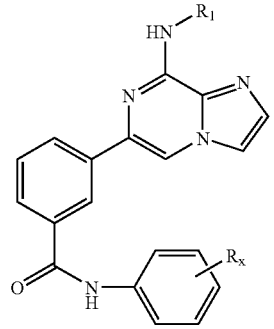

The 6-bromo imidazo[1,2-a]pyrazine compounds disclosed in Examples 1-6 may be used as starting materials in any of the reactions shown in Schemes I-III to provide compounds of Formula I.

Example 1

Preparation of [6-(3-Amino-phenyl)-imidazo[1,2-a]pyrazin-8-yl]-(1H-indozol-5-yl)-amine Step 1. 6,8-Dibromoimidazo[1,2-a]pyrazine (3)

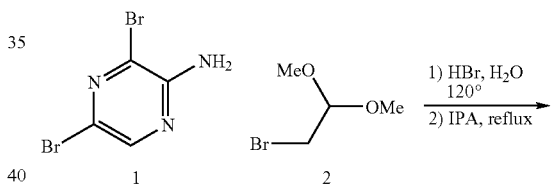

A mixture of bromoacetaldehyde diethyl acetal (51 grams (g)), 48% hydrobromic acid (HBr) (11 milliliters (mL)), and water (11 mL) is heated at 1200 for 1 hour (hr). The solution is cooled, poured into a mixture of sodium bicarbonate (NaHCO$_3$) (60 g) and isopropyl alcohol (EPA) (200 mL), and stirred for 0.5 hr. The mixture is filtered, and the filtrate is treated with 3,5-dibromo-2-aminopyrazine (1) (33 g) and heated under reflux for 16 hr. The suspension is cooled in ice, treated with 48% HBr (3 mL) and diethyl ether (60 mL) and filtered to afford (3) as the hydrobromide salt.

Step 2. (6-Bromo-imidazo[1,2-a]pyrazin-8-yl)-(1H-indazol-5-yl)-amine (4)

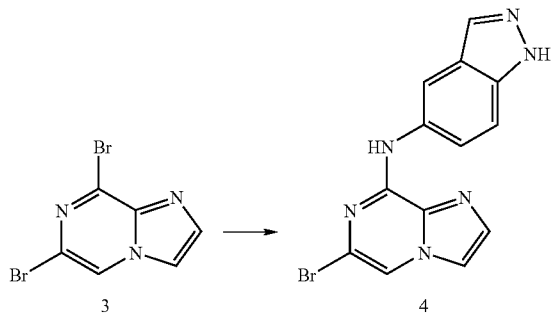

A mixture of 1.00 equivalent (eq.) of 6,8-dibromo-imidazo[1,2-a]pyrazine and 1.00 eq. of 1H-Indazol-5-ylamine are dissolved in acetonitrile and placed into a sealed tube and heated at 100° C. for 24 hours. The mixture is cooled to room temperature (RT) and partitioned between ethyl acetate (EtOAc) and saturated (sat.) $NaHCO_3$. The aqueous phase is extracted with EtOAc and combined extracts are dried over $Na_2SO_4$. The solvent is removed under reduced pressure and the resulting residue is purified by flash chromatography (EtOAc) to yield (4).

Step 3. [6-(3-Amino-phenyl)-imidazo[1,2-a]pyrazin-8-yl]-(1H-indazol-5-yl)-amine (5)

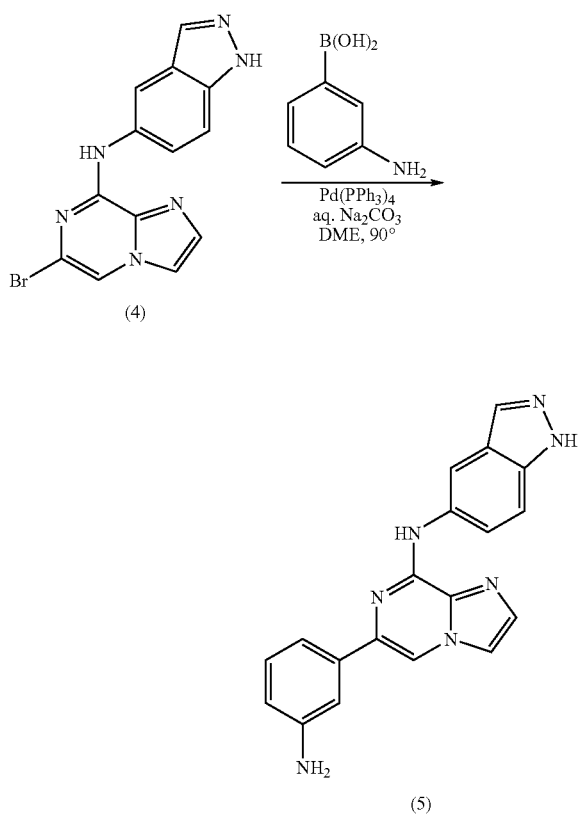

A mixture of 1.00 eq. of (6-Bromo-imidazo[1,2-a]pyrazin-8-yl)-(1H-indazol-5-yl)-amine, 1.1 eq. of $R_4$-substituted boronic acid, and 0.10 eq. of $Pd(PPh_3)_4$, 2.2 eq. of $K_3PO_4$ in 4:1 1,4-dioxane:water is heated to 90° C. for 24 hr. The mixture is cooled to RT and partitioned between EtOAc and sat. $NaHCO_3$. The aqueous phase is extracted with EtOAc and combined extracts are dried over $Na_2SO_4$. The solvent is removed under reduced pressure and the resulting residue is purified by flash chromatography (EtOAc) to yield (5).

Step 4. 4-tert-Butyl-N-{3-[8-(1H-indazol-5-ylamino)-imidazo[1,2-a]pyrazin-6-yl]-phenyl}-benzamide (6)

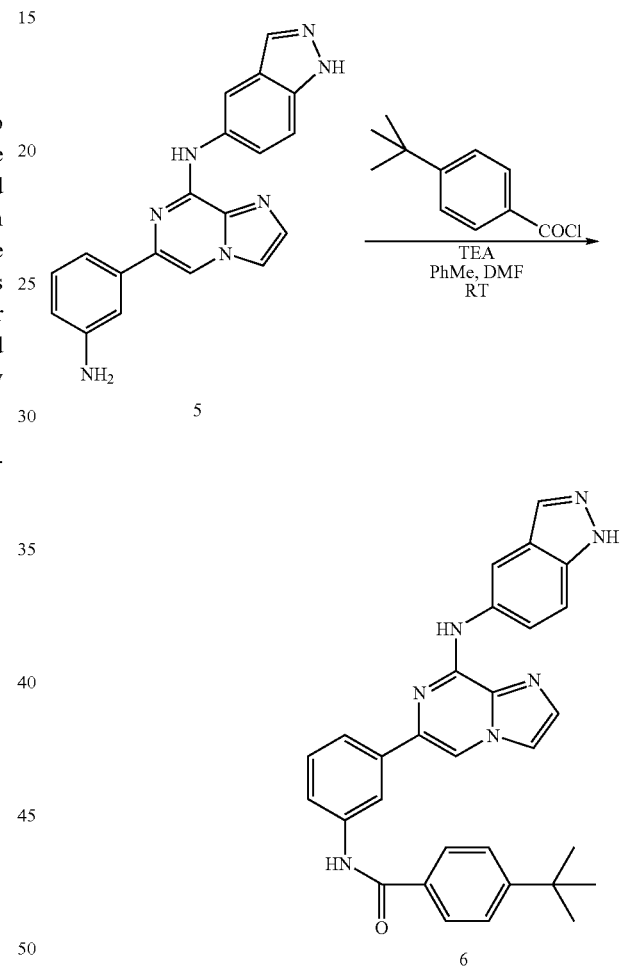

A solution of 1.00 eq. of [6-(3-amino-phenyl)-imidazo[1,2-a]pyrazin-8-yl]-(1H-indazol-5-yl)-amine b in toluene is treated dropwise with 1.00 eq. of aryl chloride and stirred at RT for 24 hr. The resulting mixture is partitioned between EtOAc/saturated $NaHCO_3$. The aqueous phase is extracted with EtOAc and the combined extracts are dried over $Na_2SO_4$. The solvent is removed under reduced pressure and the resulting residue is purified by flash chromatography (EtOAc) to yield 4-tert-Butyl-N-{3-[8-(1H-indazol-5-ylamino)-imidazo[1,2-a]pyrazin-6-yl]-phenyl}-benzamide (6) MF=$C_{30}H_{27}N_7O$, MW=501.58, Mass Spec m/z ($M^+$+1) 502.28. This compound was tested in the Btk biochemical assay of Example 7, below, and found to have an $IC_{50}$ value of less than 1 micromolar.

Example 2

Preparation of 4-tert-Butyl-N-{3-[8-(1H-indol-6-ylamino)-imidazo[1,2-a]pyrazin-6-yl]-phenyl}-benzamide Step 1. (6-Bromo-imidazo[1,2-a]pyrazin-8-yl)-(1H-indol-6-yl)-amine

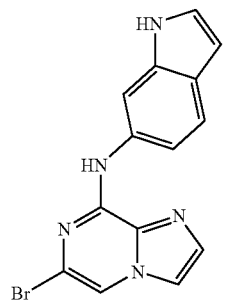

A quantity of 0.23 g (1 mmole) of 6-Amino-indole-1-carboxylic acid tert-butyl ester is treated with 0.27 g (1 mmole) of 6,8-Dibromo-imidazo[1,2-a]pyrazine in acetonitrile with 3 eq. of $K_2CO_3$ at reflux for 16 hrs. The reaction mixture is cooled partitioned between ethyl acetate and water, the organic extracts are dried over anhydrous $MgSO_4$ and evaporated in vacuo to afford 6-(6-Bromo-imidazo[1,2-a]pyrazin-8-ylamino)-indole-1-carboxylic acid tert-butyl ester. 6-(6-Bromo-imidazo[1,2-a]pyrazin-8-ylamino)-indole-1-carboxylic acid tert-butyl ester is treated with an excess of TFA in dichloromethane at room temperature for 2 hrs. The reaction solution is evaporated in vacuo and partitioned between saturated $Na_2CO_3$ and ethyl acetate; the organic extracts are dried over anhydrous $MgSO_4$ and evaporated in vacuo to afford (6-Bromo-imidazo[1,2-a]pyrazin-8-yl)-(1H-indol-6-yl)-amine.

Step 2. [6-(3-Amino-phenyl)-imidazo[1,2-a]pyrazin-8-yl]-(1H-indol-6-yl)-amine

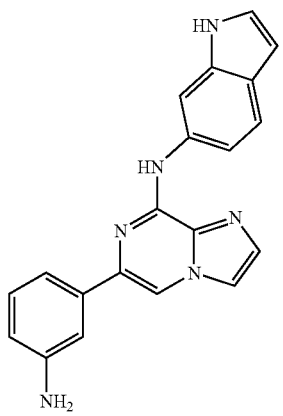

A quantity of 0.33 g (1 mmole) of (6-bromo-imidazo[1,2-a]pyrazin-8-yl)-(1H-indol-6-yl)-amine is dissolved in 10 mL ethylene glycol dimethyl ether and the solution purged for 15 minutes with $N_2$. Catalytic tetrakis(triphenylphosphine)palladium (10 mol %) is added and the solution purged with $N_2$ for 5 minutes with vigorous stirring. 3-Aminophenylboronic acid hemisulfate (0.23 g, 1.25 mmole) is added to the reaction, followed by 4 mL of 1.0N $Na_2CO_3$. The reaction is heated to 95° C. overnight in a sealed tube. The reaction is then cooled to rt, and the bilayer partitioned between ethyl acetate and water. The water layer is further extracted with ethyl acetate, and the organic extracts are pooled and washed with brine. After drying the organic extracts with solid sodium sulfate, the solvents are removed in vacuo to afford the crude [6-(3-amino-phenyl)-imidazo[1,2-a]pyrazin-8-yl]-(1H-indol-6-yl)-amine, which is purified by silica chromatography.

Step 3. 4-tert-Butyl-N-{3-[8-(1H-indol-6-ylamino)-imidazo[1,2-a]pyrazin-6-yl]-phenyl}-benzamide

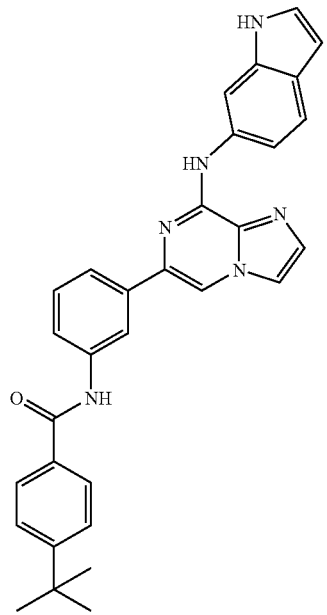

After dissolving 0.34 g (1 mmole) [6-(3-amino-phenyl)-imidazo[1,2-a]pyrazin-8-yl]-(1H-indol-6-yl)-amine in 20 mL anhydrous THF, 3 equivalents of triethylamine are added and the reaction solution is cooled to 0° C. A solution of 0.2 g of 4-tert-butyl-benzoyl chloride (1 mmole) in 5 mL THF is added dropwise to the 0° C. reaction solution under $N_2$. The ice bath is removed and the reaction is allowed to warm slowly to rt for 1 hr. Diethyl ether is then added slowly to the reaction solution and the resulting solid filtered and washed with diethyl ether to provide pure 4-tert-butyl-N-{3-[8-(1H-indol-6-ylamino)-imidazo[1,2-a]pyrazin-6-yl]-phenyl}-benzamide.

Example 3

Preparation of N-{3-[8-(Benzooxazol-6-ylamino)-imidazo[1,2-a]pyrazin-6-yl]-phenyl}-4-tert-butyl-benzamide Step 1. Benzooxazol-6-yl-(6-bromo-imidazo[1,2-a]pyrazin-8-yl)-amine

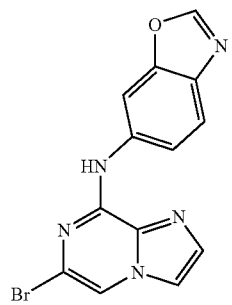

A quantity of 0.13 g (1 mmole) of Benzooxazol-6-ylamine is treated with 0.27 g (1 mmole) of 6,8-Dibromo-imidazo[1,2-a]pyrazine in acetonitrile with 3 eq of $K_2CO_3$ at reflux for 16 hrs. The reaction mixture is cooled partitioned between ethyl acetate and water, the organic extracts are dried over anhydrous $MgSO_4$ and evaporated in vacuo to afford benzooxazol-6-yl-(6-bromo-imidazo[1,2-a]pyrazin-8-yl)-amine.

Step 2. [6-(3-Amino-phenyl)-imidazo[1,2-a]pyrazin-8-yl]-benzooxazol-5-yl-amine

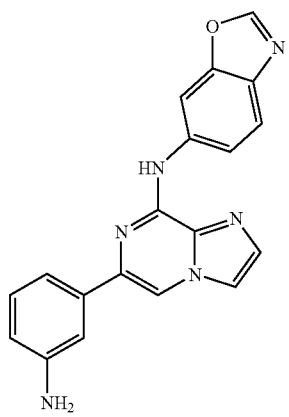

A quantity of 0.33 g (1 mmole) of benzooxazol-6-yl-(6-bromo-imidazo[1,2-a]pyrazin-8-yl)-amine is dissolved in 10 mL ethylene glycol dimethyl ether and the solution purged for 15 minutes with $N_2$. Catalytic tetrakis(triphenylphosphine) palladium (10 mol %) is added and the solution purged with $N_2$ for 5 minutes with vigorous stirring. 3-Aminophenylboronic acid hemisulfate (0.23 g, 1.25 mmole) is added to the reaction, followed by 4 mL of 1.0N $Na_2CO_3$ and the reaction heated to 95° C. overnight in a sealed tube. The reaction is then cooled to rt, and the bilayer partitioned between ethyl acetate and water. The water layer is further extracted with ethyl acetate, and the organic extracts are pooled and washed with brine. After drying the organic extracts with solid sodium sulfate, the solvents are removed in vacuo to afford the [6-(3-amino-phenyl)-imidazo[1,2-a]pyrazin-8-yl]-benzooxazol-5-yl-amine, which is purified by silica chromatography.

Step 3. N-{3-[8-(Benzooxazol-6-ylamino)-imidazo[1,2-a]pyrazin-6-yl]-phenyl}-4-tert-butyl-benzamide

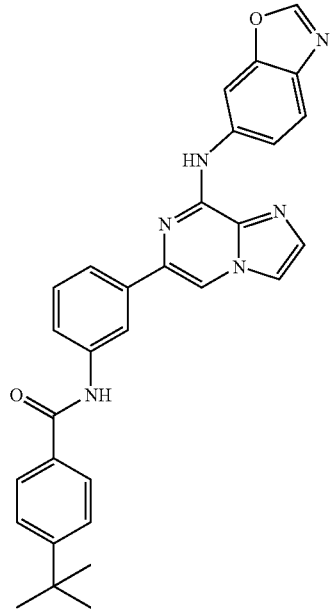

After dissolving 0.34 g (1 mmole) [6-(3a-phenyl)-imidazo[1,2-a]pyrazin-8-yl]-benzooxazol-5-yl-amine in 20 mL anhydrous THF, 3 equivalents of triethylamine are added and the reaction solution is cooled to 0° C. A solution of 0.2 g of 4-tert-butyl-benzoyl chloride (1 mmole) in 5 mL THF is added dropwise to the 0° C. reaction solution under $N_2$. The ice bath is removed and the reaction is allowed to warm slowly to rt for 1 hr. Diethyl ether is then added slowly to the reaction solution and the resulting solid filtered and washed with diethyl ether to provide pure N-{3-[8-(Benzooxazol-6-ylamino)-imidazo[1,2-a]pyrazin-6-yl]-phenyl}-4-tert-butyl-benzamide.

Example 4

Preparation of N-{3-[8-(Benzo[d]isoxazol-6-ylamino)-imidazo[1,2-a]pyrazin-6-yl]-phenyl}-4-tert-butyl-benzamide Step 1. Benzo[d]isoxazol-6-yl-(6-bromo-imidazo[1,2-a]pyrazin-8-yl)-amine

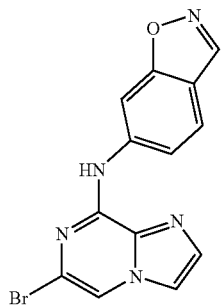

A quantity of 0.13 g (1 mmole) of Benzo[d]isoxazol-6-ylamine is treated with 0.27 g (1 mmole) of 6,8-Dibromo-imidazo[1,2-a]pyrazine in acetonitrile with 3 eq. of $K_2CO_3$ at reflux for 16 hrs. The reaction mixture is cooled partitioned between ethyl acetate and water, the organic extracts are dried over anhydrous $MgSO_4$ and evaporated in vacuo to afford Benzo[d]isoxazol-6-yl-(6-bromo-imidazo[1,2-a]pyrazin-8-yl)-amine.

Step 2. [6-(3-Amino-phenyl)-imidazo[1,2-a]pyrazin-8-yl]-benzo[d]isoxazol-6-yl-amine

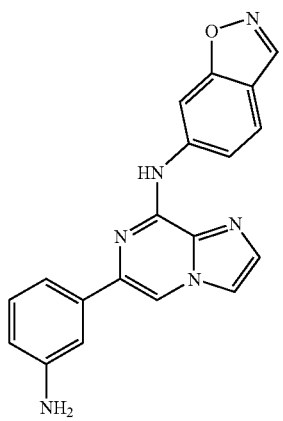

A quantity of 0.33 g (1 mmole) of benzo[d]isoxazol-6-yl-(6-bromo-imidazo[1,2-a]pyrazin-8-yl)-amine is dissolved in 10 mL ethylene glycol dimethyl ether and the solution purged for 15 minutes with $N_2$. Catalytic tetrakis(triphenylphosphine)palladium (10 mol %) is added and the solution purged with $N_2$ for 5 minutes with vigorous stirring. 3-Aminophenylboronic acid hemisulfate (0.23 g, 1.25 mmole) is added to the reaction, followed by 4 ml of 1.0N $Na_2CO_3$ and the reaction heated to 95° C. overnight in a sealed tube. The reaction is then cooled to rt, and the bilayer partitioned between ethyl acetate and water. The water layer is further extracted with ethyl acetate, and the organic extracts are pooled and washed with brine. After drying the organic extracts with solid sodium sulfate, the solvents are removed in vacuo to afford the [6-(3-amino-phenyl)-imidazo[1,2-a]pyrazin-8-yl]-benzo[d]isoxazol-6-yl-amine, which is purified by silica chromatography.

Step 3. N-{3-[8-(Benzo[d]isoxazol-6-ylamino)-imidazo[1,2-a]pyrazin-6-yl]-phenyl}-4-tert-butyl-benzamide

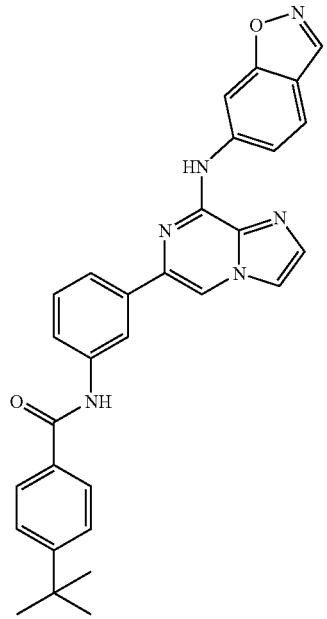

After dissolving 0.34 g (1 mmole) [6-(3-amino-phenyl)-imidazo[1,2-a]pyrazin-8-yl]-benzo[d]isoxazol-6-yl-amine in 20 mL anhydrous THF, 3 equivalents of triethylamine are added and the reaction solution is cooled to 0° C. A solution of 0.2 g of 4-tert-butyl-benzoyl chloride (1 mmole) in 5 mL THF is added dropwise to the 0° C. reaction solution under $N_2$. The ice bath is removed and the reaction is allowed to warm slowly to rt for 1 hr. Diethyl ether is then added slowly to the reaction solution and the resulting solid filtered and washed with diethyl ether to provide pure N-{3-[8-(benzo[d]isoxazol-6-ylamino)-imidazo[1,2-a]pyrazin-6-yl]-phenyl}4-tert-butyl-benzamide.

Example 5

Preparation of N-{3-[8-(Benzothiazol-6-ylamino)-imidazo[1,2-a]pyrazin-6-yl]-phenyl}-4-tert-butyl-benzamide Step 1. Benzothiazol-6-yl-(6-bromo-imidazo[1,2-a]pyrazin-8-yl)-amine

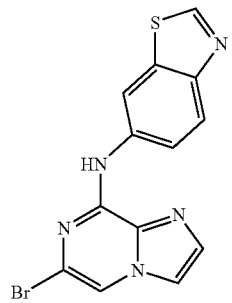

A quantity of 0.15 g (1 mmole) of benzothiazol-6-ylamine is treated with 0.27 g (1 mmole) of 6,8-Dibromo-imidazo[1,2-a]pyrazine in acetonitrile with 3 eq of $K_2CO_3$ at reflux for 16 hrs. The reaction mixture is cooled partitioned between ethyl acetate and water, the organic extracts are dried over anhydrous $MgSO_4$ and evaporated in vacuo to afford Benzothiazol-6-yl-(6-bromo-imidazo[1,2-a]pyrazin-8-yl)-amine.

Step 2. [6-(3-Amino-phenyl)-imidazo[1,2-a]pyrazin-8-yl]-benzothiazol-6-yl-amine

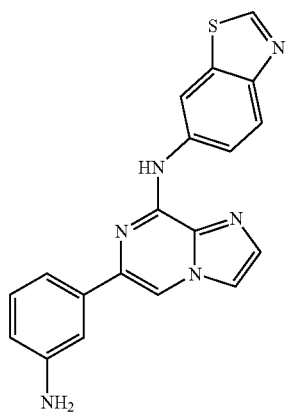

A quantity of 0.36 g (1 mmole) of benzothiazol-6-yl-(6-bromo-imidazo[1,2-a]pyrazin-8-yl)-amine is dissolved in 10 mL ethylene glycol dimethyl ether and the solution purged for 15 minutes with $N_2$. Catalytic tetrakis(triphenylphosphine) palladium (10 mol %) is added and the solution purged with $N_2$ for 5 minutes with vigorous stirring. 3-Aminophenylboronic acid hemisulfate (0.23 g, 1.25 mmole) is added to the reaction, followed by 4 mL of 1.0N $Na_2CO_3$. The reaction is heated to 95° C. overnight in a sealed tube. The reaction is then cooled to rt, and the bilayer partitioned between ethyl acetate and water. The water layer is further extracted with ethyl acetate, and the organic extracts are pooled and washed with brine. After drying the organic extracts with solid sodium sulfate, the solvents are removed in vacuo to afford the [6-(3-amino-phenyl)-imidazo[1,2-a]pyrazin-8-yl]-benzothiazol-6-yl-amine, which is purified by silica chromatography.

Step 3. N-{3-[8-(Benzothiazol-6-ylamino)-imidazo[1,2-a]pyrazin-6-yl]-phenyl}-4-tert-butyl-benzamide

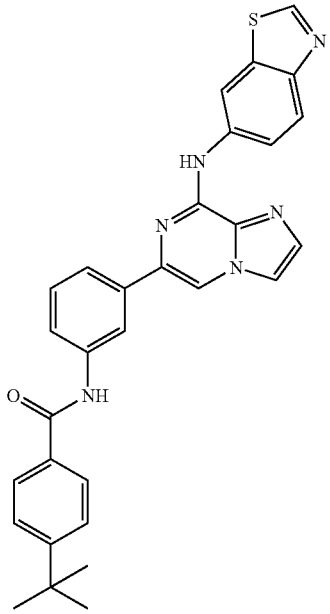

After dissolving 0.36 g (1 mmole) [6-(3-amino-phenyl)-imidazo[1,2-a]pyrazin-8-yl]-benzothiazol-6-yl-amine in 20 mL anhydrous THF, 3 equivalents of triethylamine are added and the reaction solution is cooled to 0° C. A solution of 0.2 g of 4-tert-butyl-benzoyl chloride (1 mmole) in 5 mL THF is added dropwise to the 0° C. reaction solution under $N_2$. The ice bath is removed and the reaction is allowed to warm slowly to rt for 1 hr. Diethyl ether is then added slowly to the reaction solution and the resulting solid filtered and washed with diethyl ether to provide pure N-{3-[8-(benzothiazol-6-ylamino)-imidazo[1,2-a]pyrazin-6-yl]-phenyl}-4-tert-butyl-benzamide.

Example 6

Preparation of N-{3-[8-(3H-Benzothiazol-5-ylamino)-imidazo[1,2-a]pyrazin-6-yl]-phenyl}-4-tert-butyl-benzamide Step 1. (3H-Benzoimidazol-5-yl)-(6-bromo-imidazo[1,2-a]pyrazin-8-yl)-amine

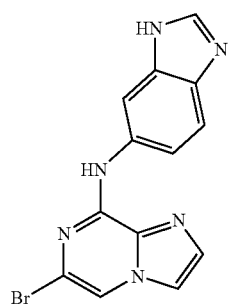

A quantity of 0.23 g (1 mmole) of 6-Amino-benzoimidazole-1-carboxylic acid tert-butyl ester is treated with 0.27 g (1 mmole) of 6,8-Dibromo-imidazo[1,2-a]pyrazine in acetonitrile with 3 eq. of $K_2CO_3$ at reflux for 16 hrs. The reaction mixture is cooled partitioned between ethyl acetate and water, the organic extracts are dried over anhydrous $MgSO_4$ and evaporated in vacuo to afford 6-(6-Bromo-imidazo[1,2-a]pyrazin-8-ylamino)-benzoimidazole-1-carboxylic acid tert-butyl ester. 6-(6-Bromo-imidazo[1,2-a]pyrazin-8-ylamino)-benzoimidazole-1-carboxylic acid tert-butyl ester is treated with an excess of TFA in dichloromethane at room temperature for 2 hrs. The reaction solution is evaporated in vacuo and partitioned between saturated $Na_2CO_3$ and ethyl acetate, the organic extracts are dried over anhydrous $MgSO_4$ and evaporated in vacuo to afford (3H-Benzoimidazol-5-yl)-(6-bromo-imidazo[1,2-a]pyrazin-8-yl)-amine.

Step 2. [6-(3-Amino-phenyl)-imidazo[1,2-a]pyrazin-8-yl]-(3H-benzoimidazol-5-yl)-amine

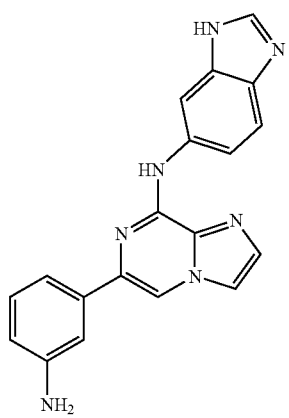

A quantity of 0.34 g (1 mmole) of (3H-benzoimidazol-5-yl)-(6-bromo-imidazo[1,2-a]pyrazin-8-yl)-amine is dissolved in 10 mL ethylene glycol dimethyl ether and the solution purged for 15 minutes with $N_2$. Catalytic tetrakis(triphenylphosphine)-palladium (10 mol %) is added and the solution purged with $N_2$ for 5 minutes with vigorous stirring. 3-Aminophenylboronic acid hemisulfate (0.23 g, 1.25 mmole) is added to the reaction, followed by 4 mL of 1.0N $Na_2CO_3$ and the reaction heated to 95° C. overnight in a sealed tube. The reaction is then cooled to rt, and the bilayer partitioned between ethyl acetate and water. The water layer is further extracted with ethyl acetate, and the organic extracts are pooled and washed with brine. After drying the organic extracts with solid sodium sulfate, the solvents are removed in vacuo to afford the [6-(3-amino-phenyl)-imidazo[1,2-a]pyrazin-8-yl]-(3H-benzoimidazol-5-yl)-amine, which is purified by silica chromatography.

Step 3. N-{3-[8-(3H-Benzoimidazol-5-ylamino)-imidazo[1,2-a]pyrazin-6-yl]-phenyl}-4-tert-butyl-benzamide

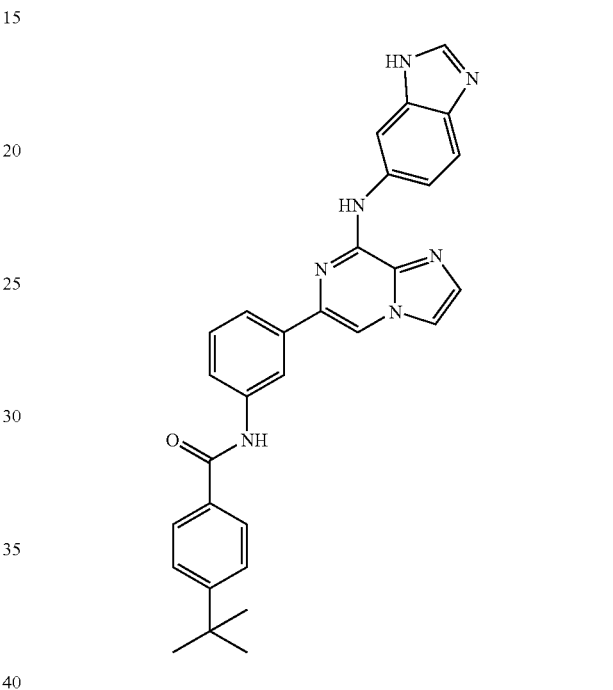

After dissolving 0.34 g (1 mmole) [6-(3-amino-phenyl)-imidazo[1,2-a]pyrazin-8-yl]-(3H-benzoimidazol-5-yl)-amine in 20 mL anhydrous THF, 3 equivalents of triethylamine are added and the reaction solution is cooled to 0° C. A solution of 0.2 g of 4-tert-butyl-benzoyl chloride (1 mmole) in 5 mL THF is added dropwise to the 0° C. reaction solution under $N_2$. The ice bath is removed and the reaction is allowed to warm slowly to rt for 1 hr. Diethyl ether is then added slowly to the reaction solution and the resulting solid filtered and washed with diethyl ether to provide pure N-{3-[8-(3H-benzoimidazol-5-ylamino)-imidazo[1,2-a]pyrazin-6-yl]-phenyl}-4-tert-butyl-benzamide.

Preferred compounds of synthetic Examples 1 to 6 tested in the Btk biochemical assay described in Example 7 exhibit an $IC_{50}$ value less than or equal to 1 micromolar. Certain more preferred compounds exhibit an $IC_{50}$ value less than or equal to 100 nM, and certain of these compounds exhibit an $IC_{50}$ value less than or equal to 10 nM in the Btk biochemical assay of Example 7. Some preferred compounds disclosed in synthetic Examples 1 to 6 exhibit an $IC_{50}$ value less than or equal to 10 micromolar when tested in the B-cell proliferation assay of Example 8, certain of these compounds exhibit an $IC_{50}$ value less than or equal to 1 micromolar, and certain of these compounds exhibit an $IC_{50}$ value less than or equal to 500 nM in this assay. Certain of these compounds do not inhibit T-cell proliferation and have $IC_{50}$ values greater than or equal to 5 micromolar when assayed under conditions described in

41

Example 10. The compounds assayed in the Example 9 and Example 10 exhibit $IC_{50}$ values for inhibition of T-cell proliferation at least 3-fold, and in some instances 5-fold, or even 10-fold greater than the $IC_{50}$ values of these compounds for inhibition of B-cell proliferation.

Example 7

Biochemical Btk Assay

A generalized procedure for one standard biochemical Btk Kinase Assay used to test compounds disclosed in this application is as follows.

A master mix minus Btk enzyme is prepared containing 1× Cell Signaling kinase buffer (25 mM Tris-HCl, pH 7.5, 5 mM □-glycerophosphate, 2 mM dithiothreitol, 0.1 mM Na3VO4, 10 mM MgCl2), 0.5 μM Promega PTK Biotinylated peptide substrate 2, and 0.01% BSA. A master mix plus Btk enzyme is prepared containing 1× Cell Signaling kinase buffer, 0.5 μM PTK Biotinylated peptide substrate 2, 0.01% BSA, and 100 ng/well (0.06 mU/well) Btk enzyme. Btk enzyme is prepared as follows: full length human wildtype Btk (accession number NM-000061) with a C-terminal V5 and 6× His tag was subcloned into pFastBac vector for making baculovirus carrying this epitope-tagged Btk. Generation of baculovirus was done based on Invitrogen's instructions detailed in its published protocol "Bac-to-Bac Baculovirus Expression Systems" (Cat. Nos. 10359-016 and 10608-016). Passage 3 virus was used to infect Sf9 cells to overexpress the recombinant Btk protein. The Btk protein was then purified to homogeneity using Ni-NTA column. The purity of the final protein preparation was greater than 95% based on the sensitive Sypro-Ruby staining. A solution of 200 μM ATP is prepared in water and adjusted to pH7.4 with 1N NaOH. A quantity of 1.25 μL of compounds in 5% DMSO is transferred to a 96-well ½ area Costar polystyrene plate. Compounds are tested singly and with an 11-point dose-responsive curve (starting concentration is 10 μM; 1:2 dilution). A quantity of 18.75 μL of master mix minus enzyme (as a negative control) and master mix plus enzyme is transferred to appropriate wells in 96-well ½ area costar polystyrene plate. 5 μL of 200 μM ATP is added to that mixture in the 96-well ½ area Costar polystyrene plate for final ATP concentration of 40 μM. The reaction is allowed to incubate for 1 hour at room temperature. The reaction is stopped with Perkin Elmer 1× detection buffer containing 30 mM EDTA, 20 nM SA-APC, and 1 nM PT66 Ab. The plate is read using time-resolved fluorescence with a Perkin Elmer Envision using excitation filter 330 nm, emission filter 665 nm, and $2^{nd}$ emission filter 615 nm. $IC_{50}$ values are subsequently calculated.

Example 8

Ramos Cell Btk Assay

Another generalized procedure for a standard cellular Btk Kinase Assay used to test compounds disclosed in this application is as follows.

Ramos cells are incubated at a density of 0.5×107 cells/ml in the presence of test compound for 1 hr at 37° C. Cells are then stimulated by incubating with 10 μg/ml anti-human IgM F(ab)$_2$ for 5 minutes at 37° C. Cells are pelleted, lysed, and a protein assay is performed on the cleared lysate. Equal protein amounts of each sample are subject to SDS-PAGE and western blotting with either anti-phosphoBtk(Tyr223) antibody (Cell Signaling Technology #3531) to assess Btk autophosphorylation or an anti-Btk antibody (BD Transduction Labs #611116) to control for total amounts of Btk in each lysate.

42

Example 9

B-cell Proliferation Assay

B-cells are purified from spleens of 8-16 week old Balb/c mice using a B-cell isolation kit (Miltenyi Biotech, Cat #130-090-862). Testing compounds are diluted in 0.25% DMSO and incubated with 2.5×10$^5$ purified mouse splenic B-cells for 30 min prior to addition of 10 μg/ml of an anti-mouse IgM antibody (Southern Biotechnology Associates Cat #1022-01) in a final volume of 100 μl. Following 24 hr incubation, 1 μCi $^3$H-thymidine is added and plates are incubated an additional 36 hr prior to harvest using the manufacturer's protocol for SPA[$^3$H] thymidine uptake assay system (Amersham Biosciences #RPNQ 0130). SPA-bead based fluorescence is counted in a microbeta counter (Wallace Triplex 1450, Perkin Elmer).

Example 10

T Cell Proliferation Assay

T cells are purified from spleens of 8-16 week old Balb/c mice using a Pan T cell isolation kit (Miltenyi Biotech, Cat #130-090-861). Testing compounds are diluted in 0.25% DMSO and incubated with 2.5×10$^5$ purified mouse splenic T cells in a final volume of 100 μl in flat clear bottom plates precoated for 90 min at 37° C. with 10 μg/ml each of anti-CD3 (BD #553057) and anti-CD28 (BD #553294) antibodies. Following 24 hr incubation, 1 μCi $^3$H-thymidine is added and plates incubated an additional 36 hr prior to harvest using the manufacturer's protocol for SPA[$^3$H] thymidine uptake assay system (Amersham Biosciences #RPNQ 0130). SPA-bead based fluorescence was counted in a microbeta counter (Wallace Triplex 1450, Perkin Elmer).

What is claimed is:
1. A compound of Formula I:

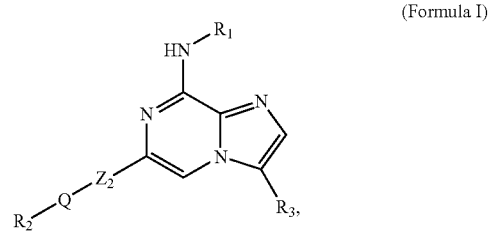

(Formula I)

wherein
R$_1$ is

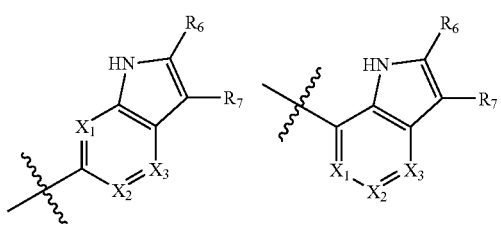

-continued

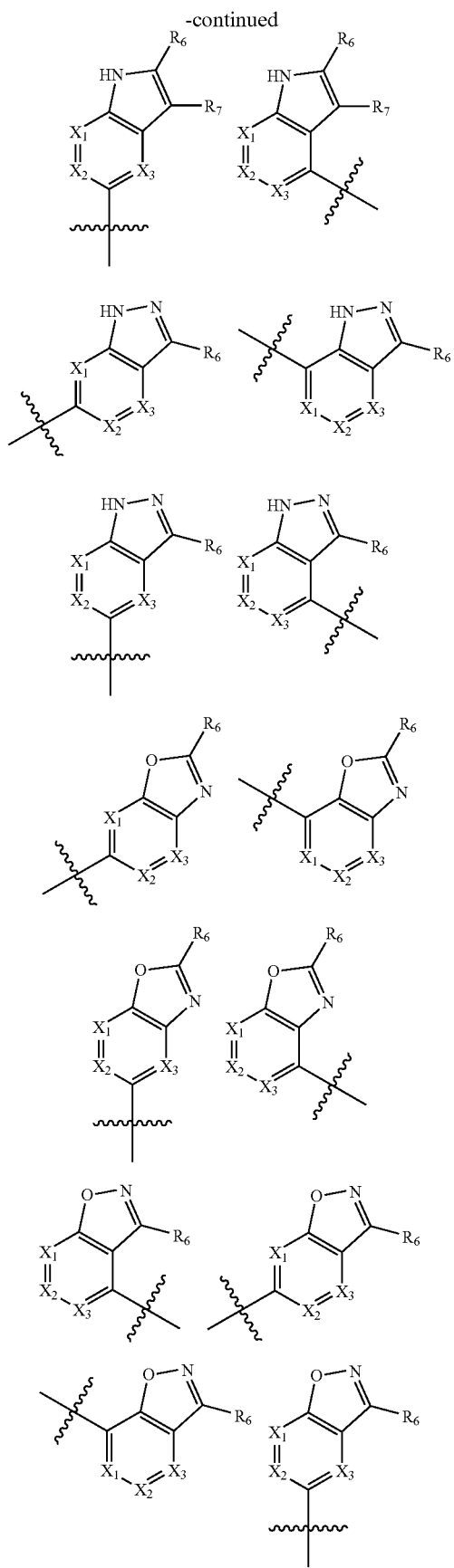

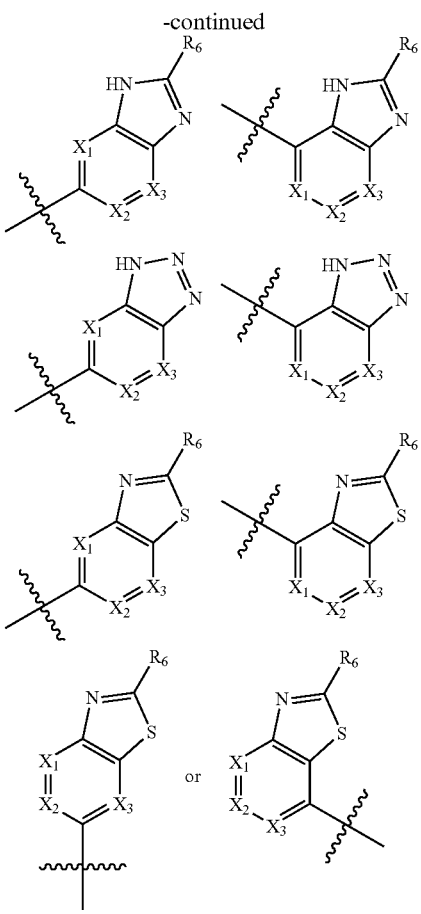

$X_1$ N or CR;
$X_2$ N or CR;
$X_3$ N or CR;
provided that at most one of $X_1$, $X_2$, and $X_3$ is N;
each R is independently hydrogen, hydroxy, cyano, halo, $C_1$-$C_2$alkyl, $C_1$-$C_2$alkoxy, $C_1$-$C_2$haloalkyl, or $C_1$-$C_2$haloalkoxy;
$Z_2$ is a divalent linking group which is para-phenylene, meta-phenylene, ortho-phenylene, or naphthylene, each of which is substituted with one group $R_2$-Q-, where
Q is

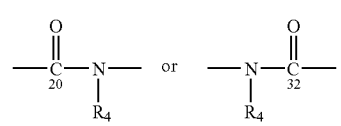

wherein
$R_4$ is
hydrogen,
$C_1$-$C_6$alkyl,
phenyl,
heteroaryl,
mono-, di-, or trisubstituted phenyl, wherein the substituents are independently hydroxy, nitro, cyano, amino, halo, —CHO, —COOH, —CONH$_2$, C$_1$-C$_6$alkyl, C$_1$-C$_6$alkoxy, C$_1$-C$_6$haloalkyl, C$_1$-C$_6$haloalkoxy, (C$_1$-C$_6$alkoxy)C$_1$-C$_6$alkoxy, mono-(C$_1$-C$_6$alkyl)amino, di-(C$_1$-C$_6$alkyl)amino, aminoC$_1$-C$_6$alkyl, C$_1$-C$_6$alkylthio, mono-(C$_1$-C$_6$alkyl)aminoC$_1$-C$_6$alkyl, di-(C$_1$-C$_6$alkyl)aminoC$_1$-C$_6$alkyl, C$_3$-C$_7$cycloalkyl, C$_2$-C$_6$alkanoyl, C$_1$-C$_6$alkoxycarbonyl, heterocycloalkyl, amido, sulfonamido, C$_2$-C$_6$alkenyl, C$_2$-C$_6$alkynyl, or heteroaryl, or mono-, di-, or trisubstituted heteroaryl, wherein the substituents are independently hydroxy, nitro, cyano, amino, halo, —CHO, —COOH, —CONH$_2$, C$_1$-C$_6$alkyl, C$_1$-C$_6$alkoxy, C$_1$-C$_6$haloalkyl, C$_1$-C$_6$haloalkoxy, (C$_1$-C$_6$alkoxy)C$_1$-C$_6$alkoxy, mono-(C$_1$-C$_6$alkyl)amino, di-(C$_1$-C$_6$alkyl)amino, aminoC$_1$-C$_6$alkyl, C$_1$-C$_6$alkylthio, mono-(C$_1$-C$_6$alkyl)aminoC$_1$-C$_6$alkyl, di-(C$_1$-C$_6$alkyl)aminoC$_1$-C$_6$alkyl, C$_3$-C$_7$cycloalkyl, C$_2$-C$_6$alkanoyl, C$_1$-C$_6$alkoxycarbonyl, heterocycloalkyl, amido, sulfonamido, C$_2$-C$_6$alkenyl, C$_2$-C$_6$alkynyl, or heteroaryl;

R$_2$ is

C$_1$-C$_7$alkyl, mono-, di-, or tri-substituted C$_1$-C$_7$alkyl, wherein the substitutents are independently hydroxy, nitro, cyano, amino, halo, —CHO, —COOH, —CONH$_2$, C$_1$-C$_6$alkyl, C$_1$-C$_6$alkoxy, C$_1$-C$_6$haloalkyl, C$_1$-C$_6$haloalkoxy, (C$_1$-C$_6$alkoxy)C$_1$-C$_6$alkoxy, mono-(C$_1$-C$_6$alkyl)amino, di-(C$_1$-C$_6$alkyl)amino, aminoC$_1$-C$_6$alkyl, C$_1$-C$_6$alkylthio, mono-(C$_1$-C$_6$alkyl)aminoC$_1$-C$_6$alkyl, di-(C$_1$-C$_6$alkyl)aminoC$_1$-C$_6$alkyl, C$_3$-C$_7$cycloalkyl, C$_2$-C$_6$alkanoyl, C$_1$-C$_6$alkoxycarbonyl, heterocycloalkyl, amido, sulfonamido, C$_2$-C$_6$alkenyl, C$_2$-C$_6$alkynyl, phenyl, or heteroaryl, C$_3$-C$_7$cycloalkyl, mono-, di-, or tri-substituted C$_3$-C$_7$cycloalkyl, wherein the substitutents are independently hydroxy, nitro, cyano, amino, halo, —CHO, —COOH, —CONH$_2$, C$_1$-C$_6$alkyl, C$_1$-C$_6$alkoxy, C$_1$-C$_6$haloalkyl, C$_1$-C$_6$haloalkoxy, (C$_1$-C$_6$alkoxy)C$_1$-C$_6$alkoxy, mono-(C$_1$-C$_6$alkyl)amino, di-(C$_1$-C$_6$alkyl)amino, aminoC$_1$-C$_6$alkyl, C$_1$-C$_6$alkylthio, mono-(C$_1$-C$_6$alkyl)aminoC$_1$-C$_6$alkyl, di-(C$_1$-C$_6$alkyl)aminoC$_1$-C$_6$alkyl, C$_3$-C$_7$cycloalkyl, C$_2$-C$_6$alkanoyl, C$_1$-C$_6$alkoxycarbonyl, heterocycloalkyl, amido, sulfonamido, C$_2$-C$_6$alkenyl, C$_2$-C$_6$alkynyl, phenyl, or heteroaryl, heterocycloalkyl, mono-, di-, or tri-substituted heterocycloalkyl, wherein the substitutents are independently hydroxy, nitro, cyano, amino, halo, —CHO, —COOH, —CONH$_2$, C$_1$-C$_6$alkyl, C$_1$-C$_6$alkoxy, C$_1$-C$_6$haloalkyl, C$_1$-C$_6$haloalkoxy, (C$_1$-C$_6$alkoxy)C$_1$-C$_6$alkoxy, mono-(C$_1$-C$_6$alkyl)amino, di-(C$_1$-C$_6$alkyl)amino, aminoC$_1$-C$_6$alkyl, C$_1$-C$_6$alkylthio, mono-(C$_1$-C$_6$alkyl)aminoC$_1$-C$_6$alkyl, di-(C$_1$-C$_6$alkyl)aminoC$_1$-C$_6$alkyl, C$_3$-C$_7$cycloalkyl, C$_2$-C$_6$alkanoyl, C$_1$-C$_6$alkoxycarbonyl, heterocycloalkyl, amido, sulfonamido, C$_2$-C$_6$alkenyl, C$_2$-C$_6$alkynyl, phenyl, or heteroaryl, C$_1$-C$_6$alkoxy, mono-, di-, or tri-substituted C$_1$-C$_6$alkoxy, wherein the substitutents are independently hydroxy, nitro, cyano, amino, halo, —CHO, —COOH, —CONH$_2$, C$_1$-C$_6$alkyl, C$_1$-C$_6$alkoxy, C$_1$-C$_6$haloalkyl, C$_1$-C$_6$haloalkoxy, (C$_1$-C$_6$alkoxy)C$_1$-C$_6$alkoxy, mono-(C$_1$-C$_6$alkyl)amino, di-(C$_1$-C$_6$alkyl)amino, aminoC$_1$-C$_6$alkyl, C$_1$-C$_6$alkylthio, mono-(C$_1$-C$_6$alkyl)aminoC$_1$-C$_6$alkyl, di-(C$_1$-C$_6$alkyl)aminoC$_1$-C$_6$alkyl, C$_3$-C$_7$cycloalkyl, C$_2$-C$_6$alkanoyl, C$_1$-C$_6$alkoxycarbonyl, heterocycloalkyl, amido, sulfonamido, C$_2$-C$_6$alkenyl, C$_2$-C$_6$alkynyl, phenyl, or heteroaryl, phenyl, mono-, di-, or trisubstituted phenyl, wherein the substituents are independently hydroxy, nitro, cyano, amino, halo, —CHO, —COOH, —CONH$_2$, C$_1$-C$_6$alkyl, C$_1$-C$_6$alkoxy, C$_1$-C$_6$haloalkyl, C$_1$-C$_6$haloalkoxy, (C$_1$-C$_6$alkoxy)C$_1$-C$_6$alkoxy, mono-(C$_1$-C$_6$alkyl)amino, di-(C$_1$-C$_6$alkyl)amino, aminoC$_1$-C$_6$alkyl, C$_1$-C$_6$alkylthio, mono-(C$_1$-C$_6$alkyl)aminoC$_1$-C$_6$alkyl, di-(C$_1$-C$_6$alkyl)aminoC$_1$-C$_6$alkyl, (C$_3$-C$_7$cycloalkyl)C$_0$-C$_2$alkyl, C$_2$-C$_6$alkanoyl, C$_1$-C$_6$alkoxycarbonyl, (heterocycloalkyl)C$_0$-C$_2$alkyl, amido, sulfonamido, C$_2$-C$_6$alkenyl, C$_2$-C$_6$alkynyl, or heteroaryl, heteroaryl, or mono-, di-, or tri-substituted heteroaryl, wherein the substituents are independently hydroxy, nitro, cyano, amino, halo, —CHO, —COOH, —CONH$_2$, C$_1$-C$_6$alkyl, C$_1$-C$_6$alkoxy, C$_1$-C$_6$haloalkyl, C$_1$-C$_6$haloalkoxy, (C$_1$-C$_6$alkoxy)C$_1$-C$_6$alkoxy, mono-(C$_1$-C$_6$alkyl)amino, di-(C$_1$-C$_6$alkyl)amino, aminoC$_1$-C$_6$alkyl, C$_1$-C$_6$alkylthio, mono-(C$_1$-C$_6$alkyl)aminoC$_1$-C$_6$alkyl, di-(C$_1$-C$_6$alkyl)aminoC$_1$-C$_6$alkyl, (C$_3$-C$_7$cycloalkyl)C$_0$-C$_2$alkyl, C$_2$-C$_6$alkanoyl, C$_1$-C$_6$alkoxycarbonyl, (heterocycloalkyl)C$_0$-C$_2$alkyl, amido, sulfonamido, C$_2$-C$_6$alkenyl, C$_2$-C$_6$alkynyl, or heteroaryl;

R$_3$ is hydrogen, C$_1$-C$_7$alkyl, heterocycloalkyl, or C$_3$-C$_7$cycloalkyl; and R$_6$ and R$_7$ are independently hydrogen, hydroxy, cyano, halo, C$_1$-C$_2$alkyl, C$_1$-C$_2$alkoxy, C$_1$-C$_2$haloalkyl, or C$_1$-C$_2$haloalkoxy, or a pharmaceutically acceptable salt or hydrate thereof.

2. A compound of claim 1 which is 4-tert-Butyl-N-{3-[8-(1H-indazol-5-ylamino)-imidazo[1,2-a]pyrazin-6-yl]-phenyl}-benzamide or a pharmaceutically acceptable salt or hydrate thereof.

3. A compound of claim 1, wherein Z$_2$ is meta-phenylene.

4. A compound of claim 1, wherein X$_1$, X$_2$, and X$_3$ are all CR.

5. A compound of claim 1, wherein X$_1$ is N, and X$_2$ and X$_3$ are both CR.

6. A compound of claim 1, wherein X$_1$ and X$_3$ are both CR and X$_2$ is N.

7. A compound of claim 1, wherein X$_1$ and X$_2$ are both CR and X$_3$ is N.

8. A compound of claim 1, wherein each R is independently hydrogen, halo, methyl, or methoxy.

9. A compound of claim 1 wherein

R$_2$ is phenyl, mono-, di-, or trisubstituted phenyl, wherein the substituents are independently hydroxy, nitro, cyano, amino, halo, —CHO, —COOH, —CONH$_2$, C$_1$-C$_6$alkyl, C$_1$-C$_6$alkoxy, C$_1$-C$_6$haloalkyl, C$_1$-C$_6$haloalkoxy, (C$_1$-C$_6$alkoxy)C$_1$-C$_6$alkoxy, mono-(C$_1$-C$_6$alkyl)amino, di-(C$_1$-C$_6$alkyl)amino, aminoC$_1$-C$_6$alkyl, C$_1$-C$_6$alkylthio, mono-(C$_1$-C$_6$alkyl)aminoC$_1$-C$_6$alkyl, di-(C$_1$-C$_6$alkyl)aminoC$_1$-C$_6$alkyl, (C$_3$-C$_7$cycloalkyl)C$_0$-C$_2$alkyl, C$_2$-C$_6$alkanoyl, C$_1$-C$_6$alkoxycarbonyl, (heterocycloalkyl)C$_0$-C$_2$alkyl, amido, sulfonamido, C$_2$-C$_6$alkenyl, C$_2$-C$_6$alkynyl, or heteroaryl, heteroaryl, or mono-, di-, or tri-substituted heteroaryl, wherein the substituents are independently hydroxy, nitro, cyano, amino, halo, —CHO, —COOH, —CONH$_2$, C$_1$-C$_6$alkyl, C$_1$-C$_6$alkoxy, C$_1$-C$_6$haloalkyl, C$_1$-C$_6$haloalkoxy, (C$_1$-C$_6$alkoxy)C$_1$-C$_6$alkoxy, mono-(C$_1$-C$_6$alkyl)amino, di-(C$_1$-C$_6$alkyl)amino, aminoC$_1$-C$_6$alkyl, C$_1$-C$_6$alkylthio, mono-(C$_1$-C$_6$alkyl)aminoC$_1$-C$_6$alkyl di-(C$_1$-C$_6$alkyl)aminoC$_1$-C$_6$alkyl, (C$_3$-C$_7$cycloalkyl)C$_0$-C$_2$alkyl, C$_2$-C$_6$alkanoyl, C$_1$-C$_6$alkoxycarbonyl, (heterocycloalkyl)C$_0$-C$_2$alkyl, amido, sulfonamido, C$_2$-C$_6$alkenyl, C$_2$-C$_6$alkynyl, or heteroaryl.

10. A compound of claim 9 wherein

R$_2$ is mono-, di-, or tri-substituted phenyl, wherein the substitutents are independently hydroxy, nitro, cyano, amino, halo, —CHO, —COOH, —CONH$_2$, C$_1$-C$_6$alkyl, C$_1$-C$_6$alkoxy, C$_1$-C$_2$haloalkyl, C$_1$-C$_2$haloalkoxy, (C$_1$-C$_6$alkoxy)C$_1$-C$_6$alkoxy, mono-(C$_1$-C$_6$alkyl)amino, di-(C$_1$-C$_6$alkyl)amino, aminoC$_1$-C$_6$alkyl, C$_1$-C$_6$alkylthio, mono-(C$_1$-C$_6$alkyl)aminoC$_1$-C$_6$alkyl, di-(C$_1$-C$_6$alkyl)aminoC$_1$-C$_6$alkyl, (C$_3$-C$_7$cycloalkyl)C$_0$-C$_2$alkyl, C$_2$-C$_6$alkanoyl, C$_1$-C$_6$alkoxycarbonyl, (heterocycloalkyl)C$_0$-C$_2$alkyl, amido, or sulfonamido, or mono-, di-, and tri-substituted pyridyl, wherein the substituents are independently hydroxy, nitro, cyano, amino, halo, —CHO, —COOH, —CONH$_2$, C$_1$-C$_6$alkyl, C$_1$-C$_6$alkoxy, C$_1$-C$_2$haloalkyl, C$_1$-C$_2$haloalkoxy, (C$_1$-C$_6$alkoxy)C$_1$-C$_6$alkoxy, mono-(C$_1$-C$_6$alkyl)amino, di-(C$_1$-C$_6$alkyl)amino, aminoC$_1$-C$_6$alkyl, C$_1$-C$_6$alkylthio, mono-(C$_1$-C$_6$alkyl)aminoC$_1$-C$_6$alkyl, di-(C$_1$-C$_6$alkyl)aminoC$_1$-C$_6$alkyl, (C$_3$-C$_7$cycloalkyl)C$_0$-C$_2$alkyl, C$_2$-C$_6$alkanoyl, C$_1$-C$_6$alkoxycarbonyl, (heterocycloalkyl)C$_0$-C$_2$alkyl, amido, or sulfonamido.

11. A compound of claim 9 wherein

R$_2$ is mono-, di-, or tri-substituted phenyl, wherein the substitutents are independently hydroxy, cyano, nitro, halo, C$_1$-C$_2$alkyl, C$_1$-C$_2$alkoxy, C$_1$-C$_2$haloalkyl, C$_3$-C$_7$cycloalkyl, (C$_3$-C$_7$cycloalkyl)methyl, heterocycloalkyl, (heterocycloalkyl)methyl, or C$_1$-C$_2$haloalkoxy; or mono-, di, or tri-substituted pyridyl, wherein the substituents are independently hydroxy, cyano, nitro, halo, C$_1$-C$_2$alkyl, C$_1$-C$_2$alkoxy, C$_1$-C$_2$haloalkyl, C$_3$-C$_7$cycloalkyl, (C$_3$-C$_7$cycloalkyl)methyl, heterocycloalkyl, (heterocycloalkyl)methyl, or C$_1$-C$_2$haloalkoxy.

12. A compound of claim 9 wherein R$_2$ is mono-, di-, or tri-substituted phenyl, wherein the substitutents are independently cyano, nitro, halo, methyl, methoxy, trifluoromethyl, or trifluoromethoxy, or mono-, di-, or tri-substituted pyridyl, wherein the substituents are independently cyano, nitro, halo, methyl, methoxy, trifluoromethyl, or trifluoromethoxy.

13. A compound of claim 9 wherein R$_2$ is phenyl or pyridyl.

14. A compound of claim 1, wherein R$_4$ is hydrogen or methyl.

15. A compound of claim 1, wherein R$_3$ is hydrogen or C$_1$-C$_4$alkyl.

16. A compound of claim 15, wherein R$_3$ is hydrogen.

17. A compound of claim 1, wherein R$_6$ and R$_7$ are each independently hydrogen, halo, cyano, C$_1$-C$_2$alkyl, C$_1$-C$_2$alkoxy, trifluoromethyl, or trifluoromethoxy.

18. A compound of claim 1, wherein R$_1$ is

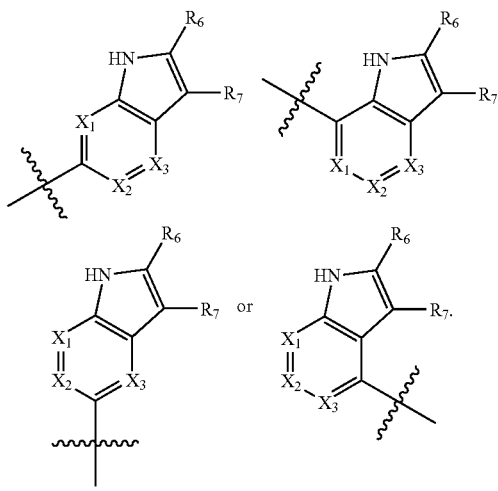

19. A compound of claim 18, wherein R$_1$ is

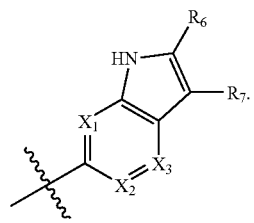

20. A compound of claim 1, wherein R$_1$ is

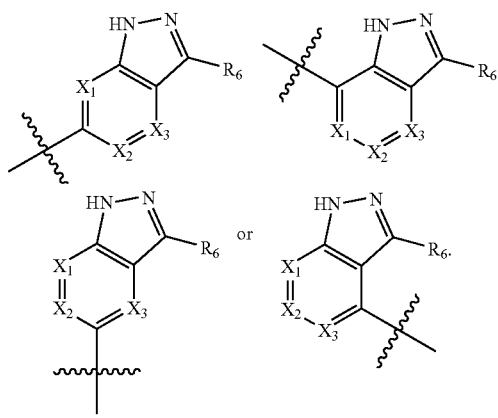

21. A compound of claim 20 wherein R$_1$ is

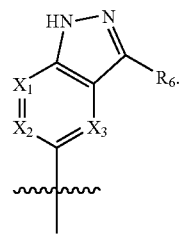

22. A compound of claim 1, wherein R$_1$ is
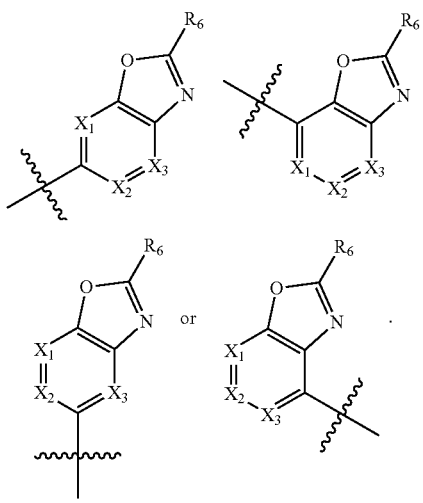
23. A compound of claim 22 wherein R$_1$ is
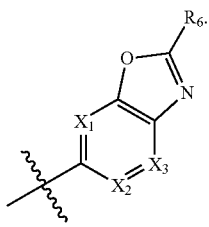
24. A compound of claim 1, wherein R$_1$ is
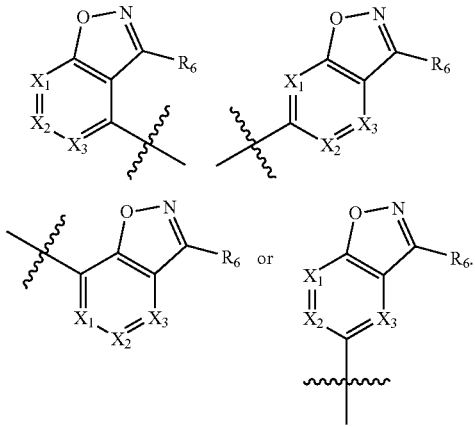
25. A compound of claim 24 wherein R$_1$ is
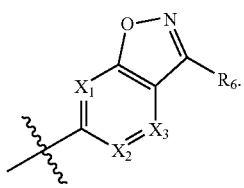
26. A compound of claim 1, wherein R$_1$ is
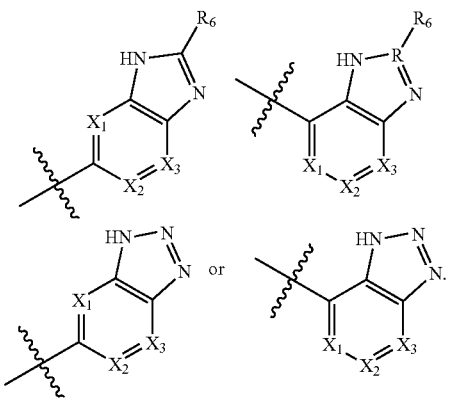
27. A compound of claim 26 wherein R$_1$ is
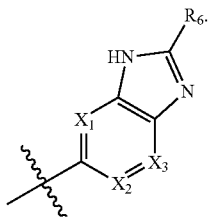
28. A compound of claim 1, wherein R$_1$ is
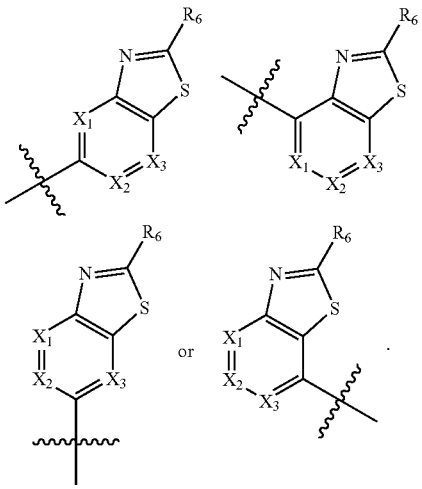
29. A compound of claim 28 wherein R$_1$ is
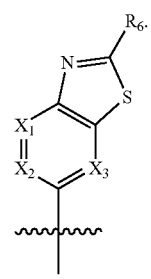

30. A compound of claim 18, wherein $X_1$, $X_2$, and $X_3$ are all CR.

31. A compound of claim 30 wherein $X_1$, $X_2$, and $X_3$ are all CH.

32. A compound of claim 1, which exhibits an $IC_{50}$ of 1 micromolar or less in an in vitro biochemical assay of Btk activity.

33. A compound of claim 32, which exhibits an $IC_{50}$ of 100 nanomolar or less in an in vitro biochemical assay of Btk activity.

34. A compound of claim 32, which exhibits an $IC_{50}$ of 10 nanomolar or less in an in vitro biochemical assay of Btk activity.

35. A compound of claim 1, which exhibits an $IC_{50}$ of 10 micromolar or less in an assay for inhibition of B-cell proliferation.

36. A compound of claim 35 which exhibits an $IC_{50}$ of 1 micromolar or less in an assay for inhibition of B-cell proliferation.

37. A compound of claim 35 which exhibits an $IC_{50}$ of 500 nanomolar or less in an assay for inhibition of B-cell proliferation.

38. A compound of claim 1, which exhibits an $IC_{50}$ value in an assay for inhibition of T-cell proliferation that is at least 3-fold greater than an $IC_{50}$ value the compound exhibits in an assay for inhibition of B-cell proliferation.

39. A compound of claim 1, wherein the compound exhibits an $IC_{50}$ value in an assay for inhibition of T-cell proliferation that is at least 5-fold greater than an $IC_{50}$ value the compound exhibits in an assay for inhibition of B-cell proliferation.

40. At least one chemical entity of claim 1, wherein the which exhibits an $IC_{50}$ value in an assay for inhibition of T-cell proliferation that is at least 10-fold greater than an $IC_{50}$ value that the compound exhibits in an assay for inhibition of B-cell proliferation.

41. A pharmaceutical composition, comprising a compound of claim 1, together with at least one pharmaceutically acceptable carrier or excipient.

42. A pharmaceutical composition of claim 41, wherein the composition is formulated as an injectable fluid, an aerosol, a cream, a gel, a tablet, a pill, a capsule, a syrup, an ophthalmic solution, or a transdermal patch.

43. A method for treating a patient having X-linked agammagolubulinemia or Wiskott-Aldrich syndrome comprising administering to the patient a therapeutically effective amount of a compound of claim 1.

44. The method of claim 43 wherein the patient is a human.

45. The method of claim 43 wherein the patient is a cat or a dog.

46. The method of claim 43 wherein the compound is administered orally.

47. The method of claim 43 wherein the compound is administered intravenously, intramuscularly, or parenterally.

48. A method for increasing sensitivity of cancer cells expressing Btk to chemotherapy, comprising administering to a patient undergoing chemotherapy with a chemotherapeutic agent an amount of a compound of claim 1, sufficient to increase the sensitivity of cancer cells to the chemotherapeutic agent.

49. A method for inhibiting B-cell proliferation comprising contacting cells expressing Btk with a compound of claim 1, in an amount sufficient to detectably decrease Btk activity in vitro.

50. A method for inhibiting ATP hydrolysis in vitro, comprising contacting cells expressing Btk with a compound of claim 1 in an amount sufficient to detectably decrease the level of ATP hydrolysis in vitro.

\* \* \* \* \*